(12) United States Patent
Boeke et al.

(10) Patent No.: US 11,624,069 B2
(45) Date of Patent: Apr. 11, 2023

(54) IN VITRO DNA SCRAMBLE

(71) Applicant: New York University, New York, NY (US)

(72) Inventors: Jef Boeke, New York, NY (US); Yi Wu, Nankai (CN)

(73) Assignee: New York University, New York, NY (US)

( * ) Notice: Subject to any disclaimer, the term of this patent is extended or adjusted under 35 U.S.C. 154(b) by 758 days.

(21) Appl. No.: 16/418,163

(22) Filed: May 21, 2019

(65) Prior Publication Data

US 2019/0382776 A1   Dec. 19, 2019

Related U.S. Application Data

(60) Provisional application No. 62/674,068, filed on May 21, 2018.

(51) Int. Cl.
*C12N 15/81* (2006.01)
*C12N 15/10* (2006.01)

(52) U.S. Cl.
CPC ......... *C12N 15/81* (2013.01); *C12N 15/1065* (2013.01)

(58) Field of Classification Search
None
See application file for complete search history.

(56) References Cited

U.S. PATENT DOCUMENTS

| | | |
|---|---|---|
| 6,379,964 B1 | 4/2002 | Del Cardayre et al. |
| 2005/0120395 A1 | 6/2005 | Burt |
| 2015/0010984 A1 | 1/2015 | Bhalla et al. |
| 2016/0046972 A1 | 2/2016 | Boeke et al. |
| 2019/0300910 A1* | 10/2019 | Shen .................... C12N 15/52 |

FOREIGN PATENT DOCUMENTS

| | | |
|---|---|---|
| WO | 2016022363 A2 | 2/2016 |
| WO | 2018009863 A1 | 1/2018 |

OTHER PUBLICATIONS

Eroshenko et al., "Mutants of Cre recombinase with improved accuracy" 4 Nature Communications 2509, 1-10 (Year: 2013).*
Dymond et al., "Synthetic chromosome arms function in yeast and generate phenotypic diversity by design," Nature, Sep. 2011, vol. 477, pp. 471-476.
Dymond et al., "The *Saccharomyces cerevisiae* SCRaMbLE system and genome minimization," Bioengineered Bugs, May 2012, vol. 3, No. 3, pp. 168-171.
Greig et al., "Hybrid Speciation in Experimental Populations of Yeast," Science, Nov. 2002, vol. 298, pp. 1773-1775.
David et al., "Advances in yeast genome engineering," FEMS Yeast Research, 2015, vol. 15, No. 1, pp. 1-14.

* cited by examiner

*Primary Examiner* — Nancy J Leith
(74) *Attorney, Agent, or Firm* — Hodgson Russ LLP

(57) ABSTRACT

Provided is an in vitro method for making a recombinant DNA molecule. The method includes combining in vitro a recombination-site-mediated evolution (a SCRaMbLE) ready DNA polynucleotide that contains at least one transcription unit (TU) and an introduced site-specific recombinase recognition sites that can be recognized by a recombinase, with a recombinase that recognizes the site-specific recombinase recognition sites. The method results in a polynucleotide that is recombined to provide a recombined polynucleotide. The method may further include determining the sequence, or determining the expression of the recombined polynucleotide. Polynucleotides made by this process, and modified yeast that contain the modified polynucleotides, are also provided.

12 Claims, 20 Drawing Sheets
(13 of 20 Drawing Sheet(s) Filed in Color)
Specification includes a Sequence Listing.

| Strain Number | Colony color | SCRaMbLEd pathway structures | Production of β-carotene (Relative to control) |
|---|---|---|---|
| yYW0257 | | | 1 |
| yYW0408 | | | 0.03 |
| yYW0213 | | | 0 |
| yYW0410 | | | 0 |
| yYW0411 | | | 0 |
| yYW0409 | | | 0 |
| yYW0404 | | | 0.83 |
| yYW0403 | | | 1.42 |
| yYW0406 | | | 1.68 |
| yYW0407 | | | 1.40 |
| yYW0401 | | | 2.06 |
| yYW0405 | | | 3.09 |
| yYW0214 | | | 2.18 |
| yYW0396 | | | 4.10 |
| yYW0212 | | | 3.50 |
| yYW0400 | | | 4.33 |
| yYW0398 | | | 4.51 |
| yYW0399 | | | 5.11 |

Figure 2

Figure 15 yYW0322 yYW0320

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: loxPsym

<400> SEQUENCE: 1
ataacttcgt ataatgtaca ttatacgaag ttat                              34

<210> SEQ ID NO 2
<211> LENGTH: 34
<212> TYPE: DNA
<213> ORGANISM: Artificial Sequence
<220> FEATURE:
<223> OTHER INFORMATION: loxPsym

<400> SEQUENCE: 2
ataacttcgt ataatgtaca ttatacgaag ttat                              34

<210> SEQ ID NO 3
<211> LENGTH: 34
<212> TYPE: DNA
<213> ORGANISM: Artificial Sequence
<220> FEATURE:
<223> OTHER INFORMATION: loxP

<400> SEQUENCE: 3
ataacttcgt ataatgtatg ctatacgaag ttat                              34

<210> SEQ ID NO 4
<211> LENGTH: 34
<212> TYPE: DNA
<213> ORGANISM: Artificial Sequence
<220> FEATURE:
<223> OTHER INFORMATION: loxP

<400> SEQUENCE: 4
ataacttcgt atagcataca ttatacgaag ttat                              34
```

IN VITRO DNA SCRAMBLE

CROSS REFERENCE TO RELATED APPLICATIONS

This application claims priority to U.S. patent application No. 62/674,068, filed May 21, 2018, the disclosure of which is incorporated herein by reference.

FIELD

This disclosure relates to a new approach for recombinant genetic engineering compositions that provide for in vitro assembly of genes or other DNA segments from a variety of sources.

SEQUENCE LISTING

The instant application contains a Sequence Listing which has been submitted in .txt format and is hereby incorporated by reference in its entirety. Said .txt copy was created on Sep. 26, 2022, is named "058636_00208_ST.txt", and is 945 bytes in size.

BACKGROUND

Use of synthetic DNA for de novo design and construction of heterologous pathways and synthetic genomes[1,2]. However, with increasing biological complexity and the number of genes in the designed system, a major challenge lies in the "debugging" process to ensure that synthetic DNA carries out the intended "designer" function(s)[3-5].

Cre/loxP is a widely used site-specific DNA recombination system derived from bacteriophage P1. Cre recombinase catalyzes a site-specific recombination reaction between two loxP sites and does not require accessory factors[6]. The loxP site is 34 bp in length, consisting of two 13 bp inverted repeats separated by an 8 bp asymmetric spacer sequence. The Cre/loxP system can be used to generate deletions, inversions, insertions (transpositions), or translocations depending on the orientation and location of loxP sites specified in a given system[7]. The simplicity of the Cre/loxP system has led to its use in both in vivo and in vitro applications. Previous in vivo applications include targeted gene knock-out, gene replacement and more[8,9], and in vitro applications comprise high-throughput DNA cloning and adenoviral vector construction[10, 11]. The general goal of most existing Cre/loxP applications is to recover a single recombination event at defined positions.

If loxP sites encode a symmetric spacer region (loxPsym), rearrangements are orientation-independent and DNA fragments between two loxPsym sites should undergo deletions or inversions with equal frequency[12,13]. The in vivo SCRaMbLE (Synthetic Chromosome Rearrangement and Modification by LoxPsym-mediated Evolution) system, built into synthetic yeast chromosomes, has been demonstrated to generate stochastic diversity in chromosome structure, including deletions, duplications, inversions, insertions (transpositions), or translocations in synthetic chromosomes synIII and synIXR[13-17]. In this system, the Cre recombinase is introduced into Sc2.0 cells genetically and controlled both transcriptionally and chemically[14, 15]. A description of in vivo in vivo SCRaMbLE is provided in PCT publication WO 2018/009863, the description of which is incorporated herein by reference. There is on ongoing need for improved compositions and methods for use SCRaMbLE related assembly of DNA segments. The present disclosure is pertinent to this need.

SUMMARY OF THE DISCLOSURE

The power of synthetic biology has enabled the expression of heterologous pathways in cells as well genome-scale synthesis projects. Together these can lead to valuable industrial applications and simultaneously build a deeper fundamental understanding of biological systems. The complexity of biological networks makes rational de novo design a grand challenge. Introducing features that confer genetic flexibility in biosynthetic pathways or genomes is a powerful strategy for downstream engineering while minimizing the number of defined design decisions made up front. The present disclosure provides an in vitro method of DNA library construction to accomplish this goal. The present 'in vitro SCRaMbLE system' uses recombinant Cre recombinase mixed in a test tube with purified DNA encoding multiple loxPsym sites. Using a β-carotene pathway designed for expression in yeast as an example, we demonstrate top-down and bottom-up in vitro SCRaMbLE enabling optimization of biosynthetic pathway flux via rearrangement of relevant transcription units. It is demonstrated that the currently provided embodiments provide improved compositions and methods to correlate phenotype and genotype. In vitro SCRaMbLE is a unique method for generating DNA libraries based on structural variation and is considered to be amenable to biochemical optimization in ways that the previously available in vivo system cannot achieve. In particular, the present disclosure provides an in vitro SCRaMbLE system, driven by recombinant Cre recombinase mixed together in a test tube or other suitable reaction container with DNA, such as isolated or purified or synthesized DNA, encoding loxPsym sites. At least two strategies using the in vitro SCRaMbLE system for pathway engineering and optimization are provided. The top-down method as described further herein comprises use of a single DNA construct encoding multiple loxPsym sites and the generation of a library of SCRaMbLEd DNA. The bottom-up system as further described herein includes an "acceptor vector" with a pool of donor fragments flanked by loxPsym sites. With the addition of Cre recombinase to the reaction, donor fragments are randomly inserted into the acceptor vector to produce a pool of diverse constructs which add one or more donor constructs to the base pathway. The products of both in vitro SCRaMbLE strategies can be transferred to a host strain directly for phenotype testing and genotyping of individual SCRaMbLE derivatives. In a non-limiting embodiment, using the β-carotene pathway in yeast as an example, it is demonstrated how these two in vitro SCRaMbLE strategies can be used for library construction and pathway optimization. Results presented herein show that in vitro SCRaMbLE is a unique method for generating DNA libraries, and is likely amenable to biochemical optimization in ways not achievable in vivo. By using the composition and methods described herein, the copy number, order and orientation of genes in an engineered pathway, and other configurations of genetic elements, can be modified using the in vitro SCRaMbLE approach, which in certain embodiments comprises an inducible evolution system that is achieved by mixing recombinant Cre recombinase with pathway components carrying loxPsym sequences under conditions that promote site specific recombination. The products may, if desired, be then transformed into yeast for pathway function testing.

It will be recognized from the present description, figures and tables, that in embodiments the disclosure comprises an in vitro method for making a recombinant DNA molecule comprising:

i) combining a recombination-site-mediated evolution (a SCRaMbLE) ready DNA polynucleotide comprising at least one transcription unit (TU), the SCRaMbLE ready DNA polynucleotide comprising introduced site-specific recombinase recognition sites that can be recognized by a recombinase, with ii) a recombinase that recognizes the site-specific recombinase recognition sites; such that the polynucleotide is recombined to provide a recombined polynucleotide; and optionally determining the sequence, and/or determining the expression of the recombined polynucleotide subsequent to introducing the recombined polynucleotide into a microorganism. In embodiments, the site-specific recombinase recognition sites are loxPsym sites, and the recombinase, such as Cre, recognizes the loxPsym sites.

In embodiments the disclosure comprises a SCRaMbLE ready DNA which comprises more than one TU. In embodiments a TU comprises a sequence that encodes a protein or a non-coding RNA. In embodiments, at least two TUs encode distinct proteins. In embodiments, the distinct proteins are enzymes, and/or participate in a same metabolic pathway and/or encode distinct proteins that form a multi-protein complex in vitro or in vivo. In embodiments, a recombinant polynucleotide obtained using a method described herein comprises an inversion and/or a deletion of a segment of the SCRaMbLE ready DNA polynucleotide that was present in the SCRaMbLE ready DNA prior to combining the SCRaMbLE ready DNA with the recombinase. In embodiments, activity of the recombinase is stopped by manipulating the in vitro reaction by application of heat or a denaturing or chelating agent. In embodiments, the disclosure includes introducing a recombined polynucleotide into a microorganism to obtain a modified microorganism, and determining function of the TUs by analysis of the modified microorganism. In embodiments, the modified microorganism is a yeast. In embodiments, a method of this disclosure further comprises determining the sequence of the recombined polynucleotide, and/or one or more functions or proteins or functional RNAs encoded by the recombined polynucleotide. The disclosure also includes a recombinant polynucleotide made by the method any method described herein, and microorganisms, such as yeast or bacteria, comprising any polynucleotide made by a method described herein.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 2. Genotype-phenotype analysis of top-down in vitro SCRaMbLEd strains. The colony pictures were taken after 3 days' incubation on SC-Ura medium. Strains derive from the experiment in FIG. 1f. The pathway structures of 17 SCRaMbLEd strains were verified by PCR analysis (FIG. 10) and Sanger sequencing of the recovered yeast plasmids. The production of β-carotene was determined by high-performance liquid chromatography (HPLC) (FIG. 11). Error bars represent standard deviation from three replicates.

FIG. 15. PCR analysis of bottom-up SCRaMbLEd constructs in yeast. All of the bottom-up SCRaMbLEd plasmids in yeast strains listed in FIG. 4 were recovered to *E. coli* for PCR analysis with the primer pairs specific for the indicated genes.

DESCRIPTION OF THE DISCLOSURE

Figure 1:
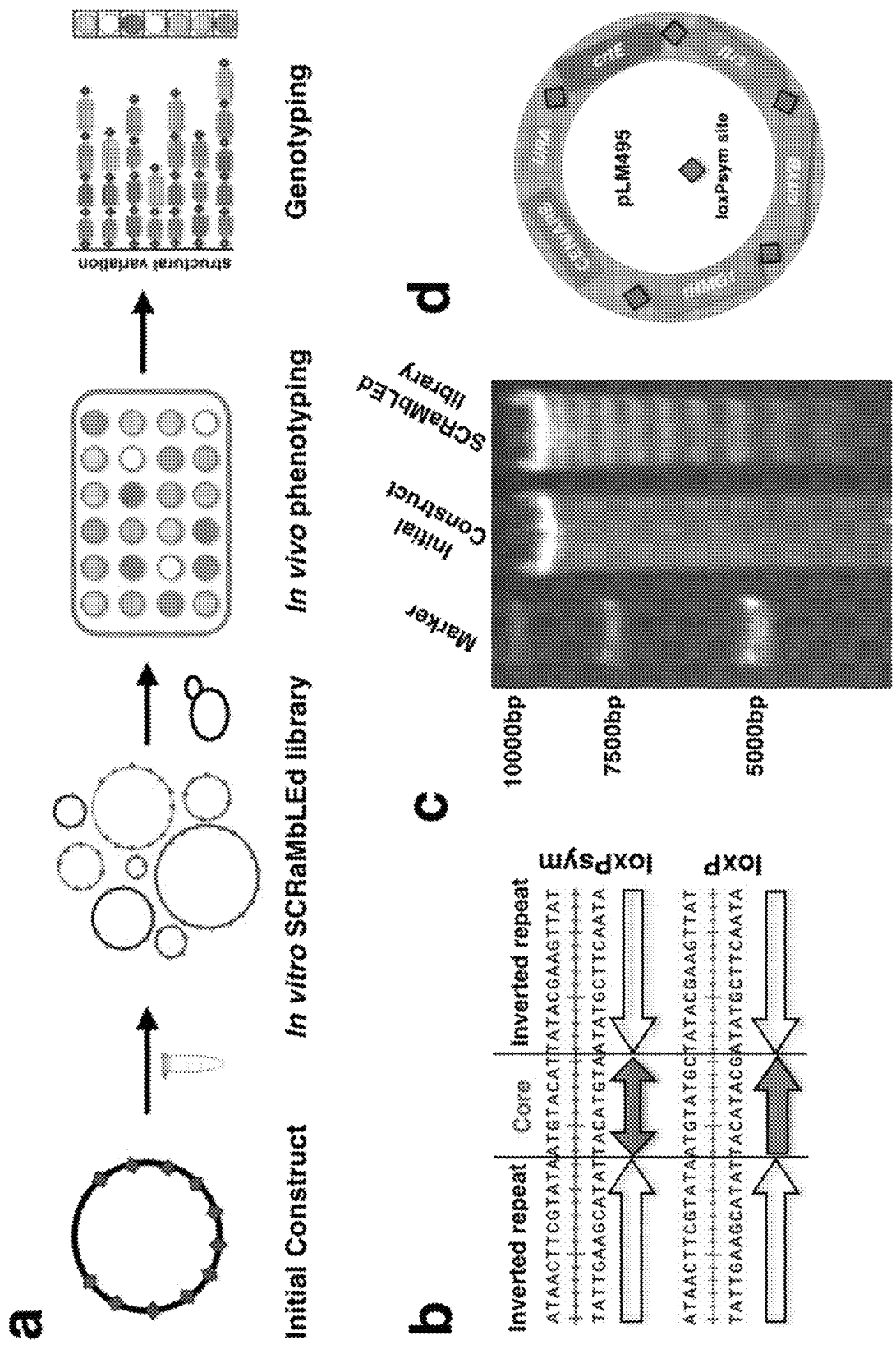
FIG. 1. Top-down in vitro SCRaMbLE. (a) Schematic of top-down in vitro SCRaMbLE. Green diamonds represent the 34 bp loxPsym site. (b) Sequence comparison between loxPsym and loxP sites. The sequence of the loxPsym site, top sequence is SEQ ID NO:1; the sequence the loxPsym site, bottom sequence SEQ ID NO:2; the sequence the loxP site, top sequence is SEQ ID NO:3; the sequence the loxPssite, bottom sequence is SEQ ID NO:4; (c) Gel electrophoresis analysis of an in vitro SCRaMbLEd library. The parental construct encoded 10 loxPsym sites with an inter-site distance of 500 bp. Material for linearization with NotI was extracted from a pool of E. coli colonies carrying the SCRaMbLEd DNA. (d) Map of pLM495. LoxPsym sites flank the β-carotene pathway genes crtE, crtI, crtYB and tHMG1. Transcription units for these genes are pTIP1-crtE-tACS2, pPGK1-crtI-tASC1, pTDH3-crtYB-tCIT1, pZEO1-tHMG1-tACS2. (e) A total of 94 unique pathway structures were determined by PacBio sequencing of a SCRaMbLEd pLM495 library. (f) Yeast colonies transformed with in vitro SCRaMbLEd pLM495. The magnified region shows different colony colors, consistent with production of colored carotenoid intermediates. Synthetic complete medium lacking uracil (SC-Ura) medium was used to select transformants.
Figure 1:
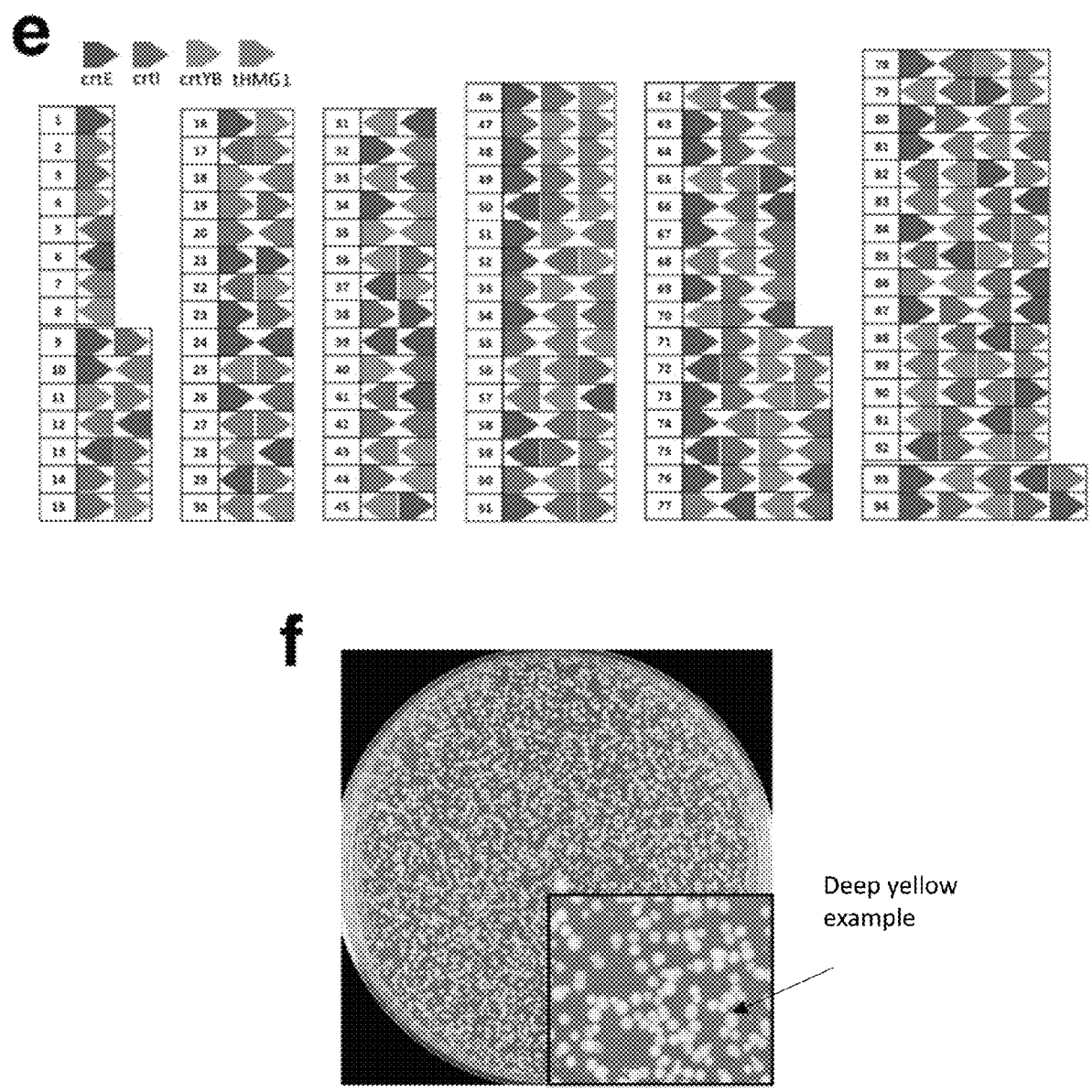

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all steps and compositions of matter described herein in the text and figures of this disclosure, including all such steps individually and in all combinations thereof, and includes all compositions of matter including but not necessarily limited to vectors, cloning intermediates, cells, and cell cultures, genetic pathways, gene and genetic element copy numbers, all in in vitro reactions and reaction components, and all combinations thereof. The disclosure can comprise or consist of any combination of these features, and any particular component, step, or combination of components and steps, can be excluded from the scope and claims of this disclosure. All polynucleotide and amino acid sequences that are referenced by way of database entry numbers, such as accession numbers, are included in this disclosure as they exist in the database as of the filing date of this application or patent. In embodiments, only one intact SCRaMbLE ready DNA polynucleotide is modified in vitro in the same reaction or series of reactions as described herein. In embodiments, more than one intact SCRaMbLE ready DNA polynucleotide is analyzed in the same or a series of reactions.

In embodiments, the disclosure includes polynucleotides that comprise a promoter sequence, a coding sequence, and a transcription termination sequence, which collectively comprise a transcription unit (TU). The TU can encode any RNA sequence, including but not necessarily limited to an RNA that encodes a protein, or a non-coding RNA, including but not limited to a functional RNA. A functional RNA can be, for example, an RNA s that can participate in CRISPR (clustered regularly interspaced short palindromic repeats) DNA or RNA editing, a snoRNA, an miRNA a ribozyme, an RNA aptamer, and other types of RNA that will be apparent from this disclosure. The RNA can be driven by any suitable promoter and transcribed by any suitable DNA polymerase, if the SCRaMbLE ready DNA polynucleotide is transcribed, whether in vitro or in vivo. Proteins encoded by TUs of this disclosure are not particularly limited, and may be any protein. In embodiments, the proteins can be enzymes, structural proteins, proteins that participate in a metabolic pathway and/or synthesis of a compound, toxins, peptides, transcription factors, receptors, receptor ligands, chemokines, protein or peptide hormones, nutritional proteins, and proteins that produce a detectable signal such as a fluorescent signal, or any other protein. In embodiments, a SCRaMbLE ready DNA polynucleotide comprises only one TU, or more than one TU, including but not limited to 1, 2, 3, 4, 5, 6, 7, 8, 9, 10, or more TUs.

In embodiments, the disclosure comprises in vitro uses of recombinases, and DNA sequences that are recognized by the recombinase. Thus, a SCRaMbLE ready DNA polynucleotide comprises at least one TU, and introduced site-specific recombinase recognition sites that can be recognized by a recombinase. The recombinase site is in various embodiments a site that is capable of being modified by the action of recombinase, which demonstrated herein using Cre recombinase and loxPsym sites, but may also be used with other recombinase and recombinase recognition sites. In certain embodiments, the recombinase recognition sequences are unique to the genome of the microorganism in which may be analyzed, i.e., they do not appear elsewhere in a host cell's genome, except as otherwise described herein. In certain approaches the disclosure comprises use of recombinase systems which may include but are not necessarily limited to Flp Recombinase which functions in the Flp/FRT system, the Dre recombinase which functions in the Dre-rox system, the Vika recombinase which functions in the Vika/vox system, Bxb 1 recombinase which functions with attP and attB sites, long terminal repeat (LTR) site-specific recombinase (Tre), and other serine recombinases, such as phiC31 integrase which mediates recombination between two 34 base pair sequences termed attachment sites (att), Hin recombinase, which recognizes 26 bp imperfect inverted repeat sequences or int2-13 each of which each recognizes distinct target sites of 39-66 bp. Further, the recombinase may be modified.

In embodiments, one or more SCRaMbLE ready DNA polynucleotide that have been processed in vitro can as described herein, if desired, be amplified and/or sequenced in vitro, and/or introduced into any suitable microorganism for further analyses, including without limitation for sequencing, analysis of RNA and/or protein expression, RNA or protein function, and for the presence or absence of any sequence or other genetic elements. Suitable microorganism may be prokaryotic or eukaryotic, the latter including but not necessarily limited to fungi, such as yeasts, including but not necessarily limited to S. cerevisiae or Sch. pombe.

In embodiments, the SCRaMbLE ready DNA polynucleotides used in this disclosure can be modified to include, if desired, genetic elements for use in in vivo screening, including but not limited to a centromere/autonomously replicating sequence (CEN/ARS), selectable markers, including but not limited to auxotrophic or other nutritional markers, antibiotic resistance, or detectable markers. Microorganisms into which the SCRaMbLE ready DNA polynucleotides are introduced can be screened to determine whether or not the SCRaMbLE ready DNA polynucleotides affect any characteristic of the microorganisms, including but not limited to growth phenotypes, reproductive fitness, synthesis of one or more compounds, detectable markers, or any other characteristic that can be influenced at least in part by the presence of the SCRaMbLE ready DNA polynucleotide.

The following examples are intended to illustrate, but not limit, the disclosure.

EXAMPLE 1

Top-Down In Vitro SCRaMbLE: Recombination Between Multiple loxPsym Sites on a Designed Construct The "top-down" in vitro SCRaMbLE system specifies use of purified Cre recombinase for rearrangement-based optimization of DNA constructs encoding multiple loxPsym sites. The loxPsym sites flank "transcription unit" (TU) sequences, the unit to be SCRaMbLEd in the system. In the presence of Cre recombinase, TUs will be randomly deleted, inverted or duplicated mediated by Cre/loxPsym reactions. Following transformation of the population of SCRaMbLEd molecules into cells, resultant phenotypes and genotypes can be evaluated and linked (FIG. 1a).

Figure 5:
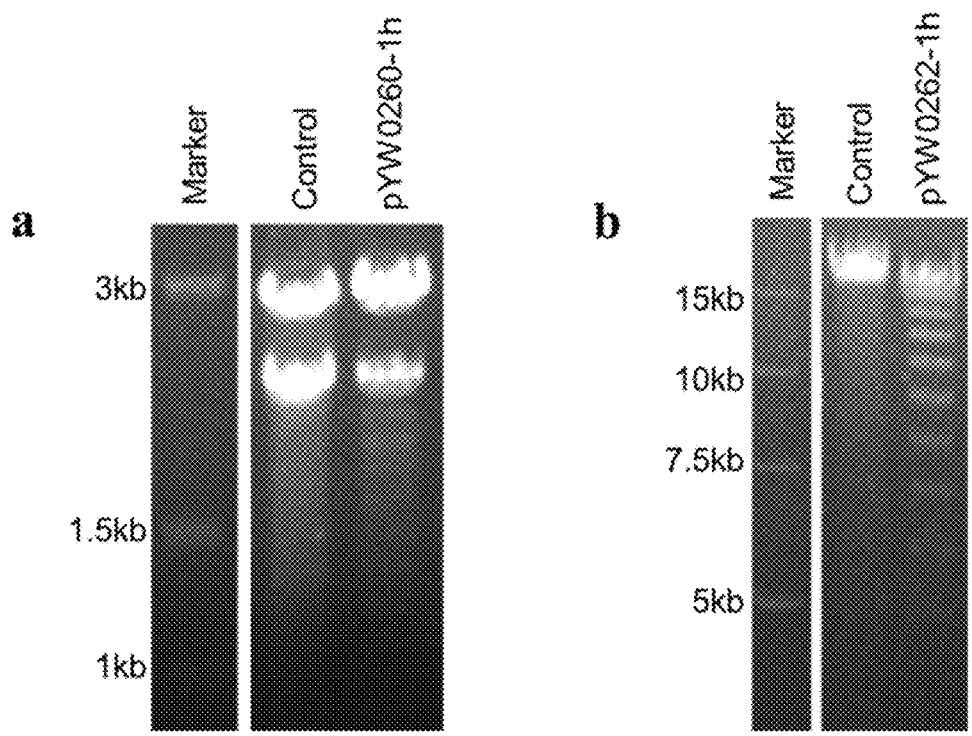
FIG. 5. In vitro SCRaMbLEing DNA constructs encoding 10 loxPsym sites. (a) The substrate DNA is a plasmid (pYW0260) encoding 10 loxPsym sites with 100 bp between adjacent loxPsym sites. The DNA for digestion was extracted from a pool of transformed *E. coli* colonies and then linearized by BamHI and BglII. (b) The substrate DNA is a plasmid (pYW0262) encoding 10 loxPsym sites with 1000 bp between adjacent loxPsym sites. The DNA for digestion was extracted from population of transformed *E. coli* colonies and then linearized by ScaI. Marker, Trans 15k DNA Marker.

To test the "chemical" feasibility of top-down in vitro SCRaMbLE, 10 loxPsym sites were evenly distributed across a 5 kb piece of DNA and assembled into a plasmid (pYW0261) by overlap PCR (FIG. 1b). After a one hour incubation with Cre recombinase, the DNA library was transformed into E. coli to more easily visualize products. To test the diversity of recovered sequences, a pool of SCRaMbLEd plasmids was extracted and then linearized for gel electrophoresis. Nine individual bands were observed, corresponding to the expected sizes for deletions between variously spaced loxPsym sites (FIG. 1c). This is consistent with no obvious preference of recombination between loxPsym sites in the system of in vitro SCRaMbLE. We observed similar results using constructs with 10 loxPsym sites spaced 100 bp and 1000 bp apart (FIG. 5).

Figure 6:
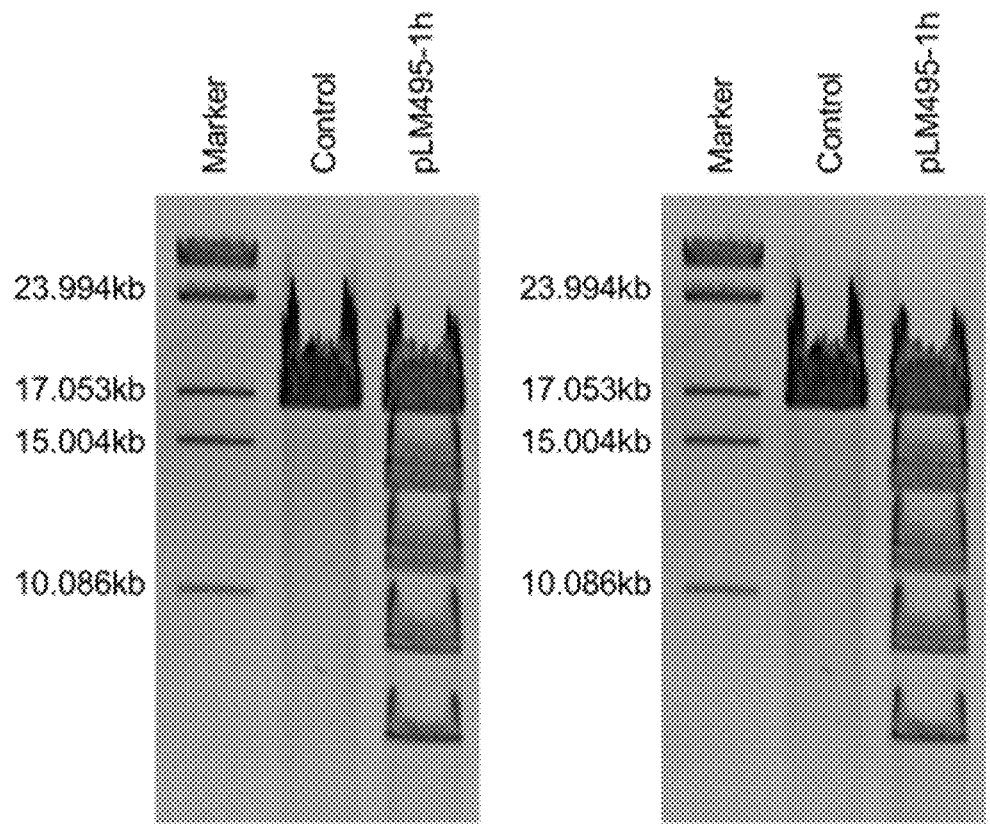
FIG. 6. Pulsed-field gel analysis of top-down in vitro SCRaMbLEd pLM495. The DNA libraries was extracted from pool of SCRaMblEd *E. coli* colonies and then linearized by NotI. Marker, Lambda DNA-Mono Cut Mix. The NotI site is encoded on the vector backbone of pLM495. pLM495 is 16.1 kb in length with inter-loxPsym distances of 2.0, 2.6, 2.8, and 2.3 kb.
Figure 7:
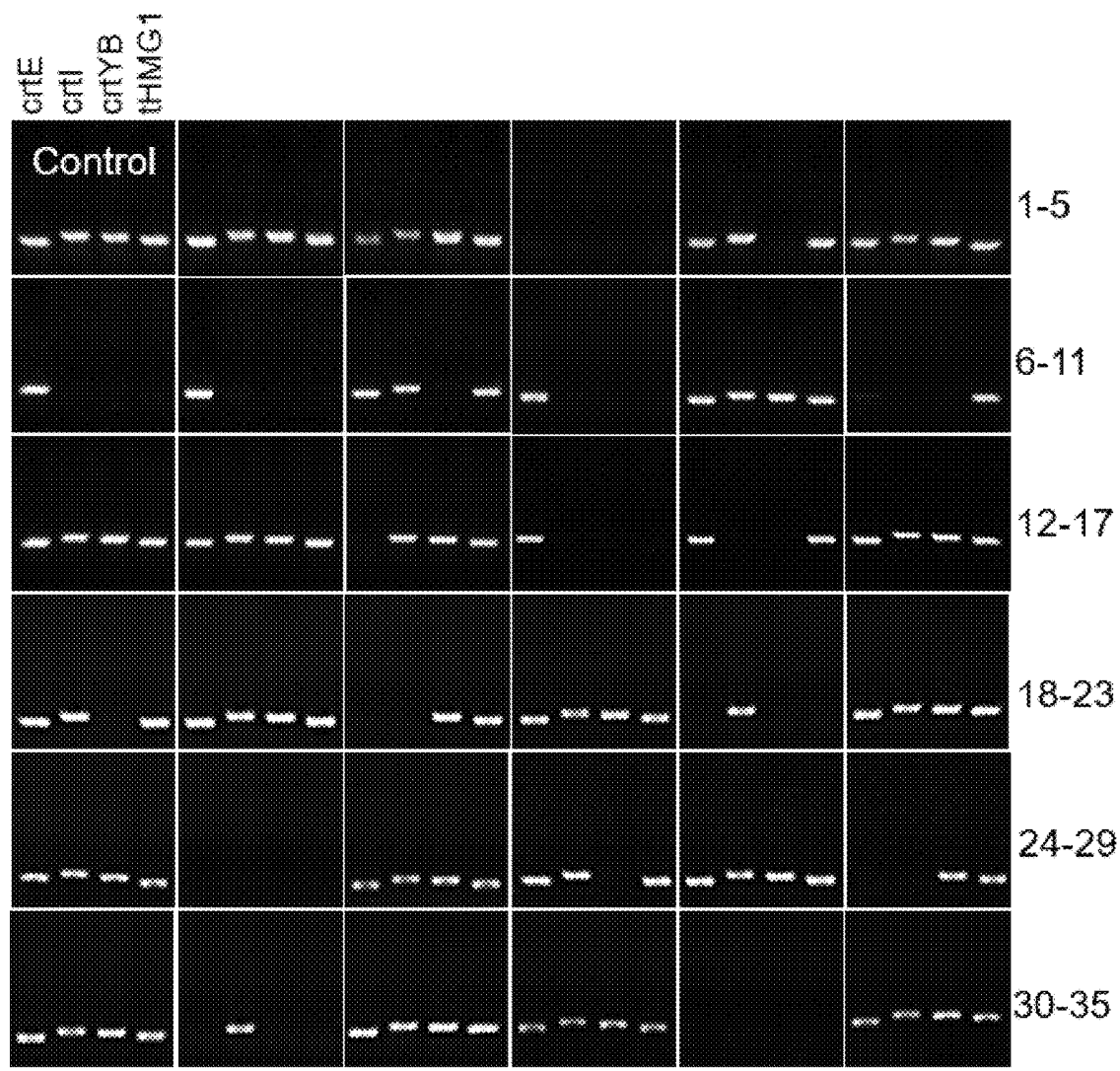
FIG. 7. PCR analysis of top-down in vitro SCRaMbLEd pLM495 to evaluate gene deletions. A total of 300 pLM495 *E. coli* strains (35 shown here) were randomly picked from in vitro SCRaMbLEd *E. coli* transformants. The control panel used purified pLM495 as template DNA.
Figure 8:
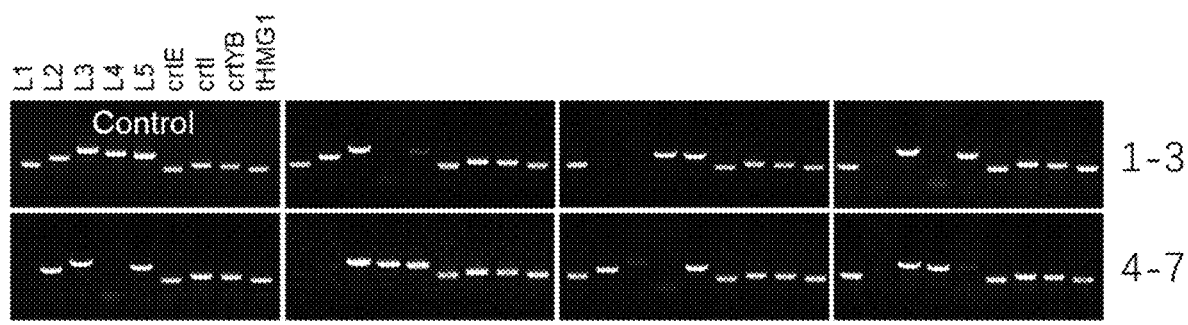
FIG. 8. PCR analysis of top-down in vitro SCRaMbLEd pLM495 to evaluate inversion frequency. A total of 100 pLM495 *E. coli* strains (7 shown here) were randomly picked from *E. coli* colonies transformed with in vitro SCRaMbLEd pLM495. L1, L2, L3, L4, L5 are specific PCR reactions designed to amplify the junction regions of vector-crtE, crtE-crtI, crtI-crtYB, crtYB-tHMG1, tHMG1-vector respectively. PCR primers for genes crtE, crtI, crtYB, tHMG1 are same as FIG. 7.
Figure 9:
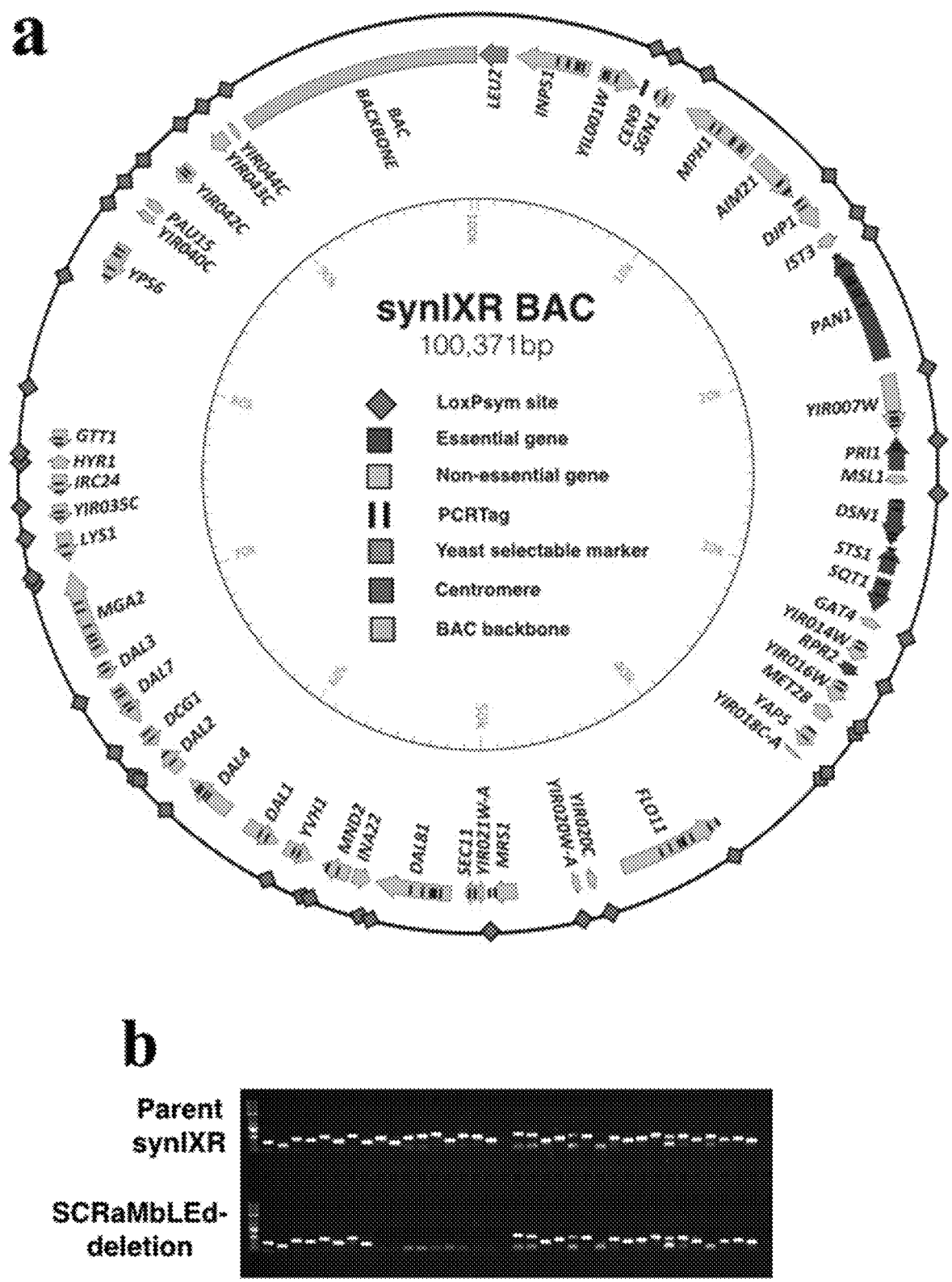
FIG. 9. Deletion frequency for top-down in vitro SCRaMbLEd synIXR-BAC. (a) Map of synIXR-BAC. A total of 43 loxPsym sites are encoded, along with 46 genes from chromosome IX (b) PCRTag analysis to evaluate deletion events following in vitro SCRaMbLE. PCRTags are designed in open reading frame to distinguish synthetic sequence from wild type sequence. The sequences of PCRTag are shown in Table 2. (c) A total of 46 *E. coli* strains were randomly picked following in vitro SCRaMbLE and transformation and subjected to qPCRTag analysis. A heatmap predicts amplification as a function of crossing point (Cp) in each of 1536 wells. Yellow, crossing point (Cp) value <23, defined as true positives; Light blue, 23<Cp Value<26, defined as false positive PCR products; Blue, CP value >26, defined as negative PCR products; Dark blue, no amplification. The positive values in the water control are likely primer dimers. PCRTags in the top (near YIL002C) and bottom (near YIR042C) are close to the vector sequence, which encodes the gene used to select *E. coli* transformants (beta lactamase) and are least frequently deleted. Details of primer sequence are listed in Table 2. (d) Deletion frequency for in vitro SCRaMbLE of plasmids with 5 or 43 loxPsym sites. PCR analysis was used to count the number of deletion events after transformation of the in vitro SCRaMbLEd pLM495 and synIXR-BAC to *E. coli* (FIG. 7, 9c).
Figure 9:
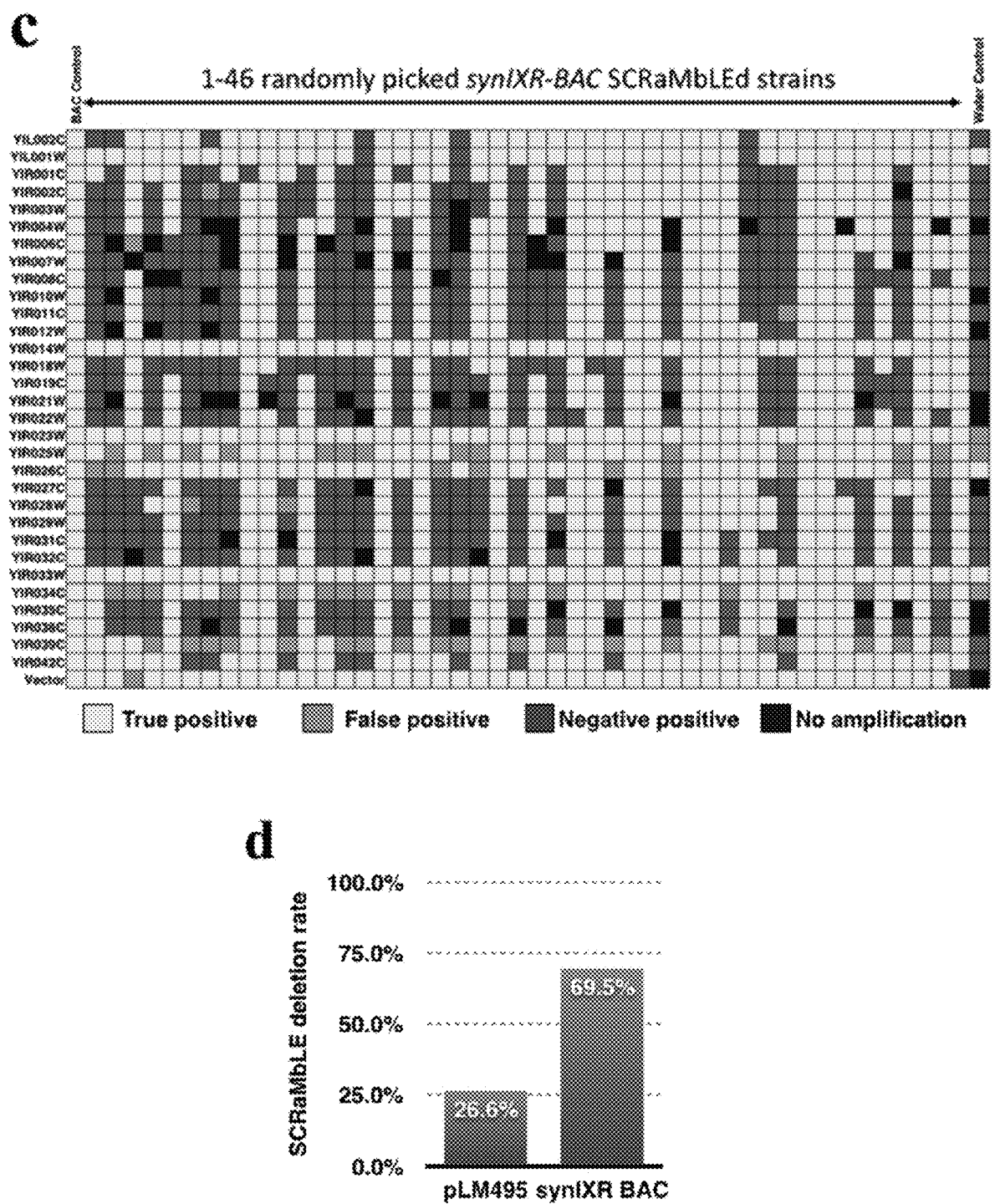

To biologically test the system, we performed an in vitro SCRaMbLE experiment with a yeast/E. coli centromeric shuttle vector (pLM495) encoding four β-carotene pathway TUs flanked by 5 loxPsym sites (FIG. 1d). In this pathway, three carotenogenic genes were sourced from the carotenoid-producing fungus Xanthophyllomyces dendrorhous (crtE, crtI, crtYB)[18] and a truncated HMG1 gene was derived from S. cerevisiae. Different promoters and terminators were selected from the S. cerevisiae genome to drive expression of each pathway gene[19]. In vitro SCRaMbLE with Cre recombinase was performed on the purified plasmid for one hour and the products were transformed to E. coli for genotypic testing. DNA purified from E. coli was subjected to digestion and pulsed-field gel analysis, which revealed diverse deletion events for SCRaMbLEd pLM495 (FIG. 6). Subsets of plasmids bearing deletions of varied length were isolated and evaluated by gel electrophoresis. To further determine the efficiency of deletions and inversions, we performed PCR analysis of individual E. coli colonies. A total of 300 colonies were randomly picked and analyzed by PCR within individual genes to evaluate deletion frequency. ~27% of the colonies carried at least one deletion event (FIG. 7). Another 100 colonies were picked and analyzed by PCR using primers spanning loxPsym sites to evaluate inversion frequency; colonies showing existence of individual genes by PCR but absence of junction regions are inferred to have undergone inversion events. ~28% of the colonies had evidence of inversion events (FIG. 8). This result of roughly equal efficiency of deletion and inversion for in vitro SCRaMbLE system is consistent with a previous report for Cre/loxPsym in vivo[12-13]. To test whether the efficiency of in vitro SCRaMbLE was related to the number of loxPsym sites in the substrate DNA, we counted and compared deletion frequencies of in vitro SCRaMbLEd pLM495 or synIXR-BAC, a previously de novo synthesized ~100 kb BAC which encodes 43 loxPsym sites (FIG. 9a)[14]1. Using PCRTag analysis[14] we observed deletions of DNA segments after in vitro SCRaMbLE (FIG. 9b). A total of 46 synIXR-BAC colonies were randomly picked for this analysis, which was carried out by real time PCR[20] (FIG. 9c). The deletion frequency for the synIXR-BAC was ~70%, which is higher than with the 5 loxPsym site plasmid pLM495 (FIG. 9d). This suggests that the number of recombination events is positively correlated with loxPsym site number.

We used a single molecule real time sequencing method (Pacific BioSystems SMRT; PacBio) to analyze the diversity of the SCRaMbLEd library recovered from E. coli. PacBio enables PCR-free long read sequencing, which is appropriate to identify structural variation in the DNA library. With only 4 genes in pLM495, a total of 94 unique constructs were detected in the SCRaMbLEd pool (FIG. 1e). Recombination between multiple loxPsym sites resulted in deletions, inversions, duplications and other complex combinational events. Considering the limited read depth and low probability of longer DNA reads, we believe that the diversity of SCRaMbLEd molecules is even higher than observed in this experiment.

Figure 10:
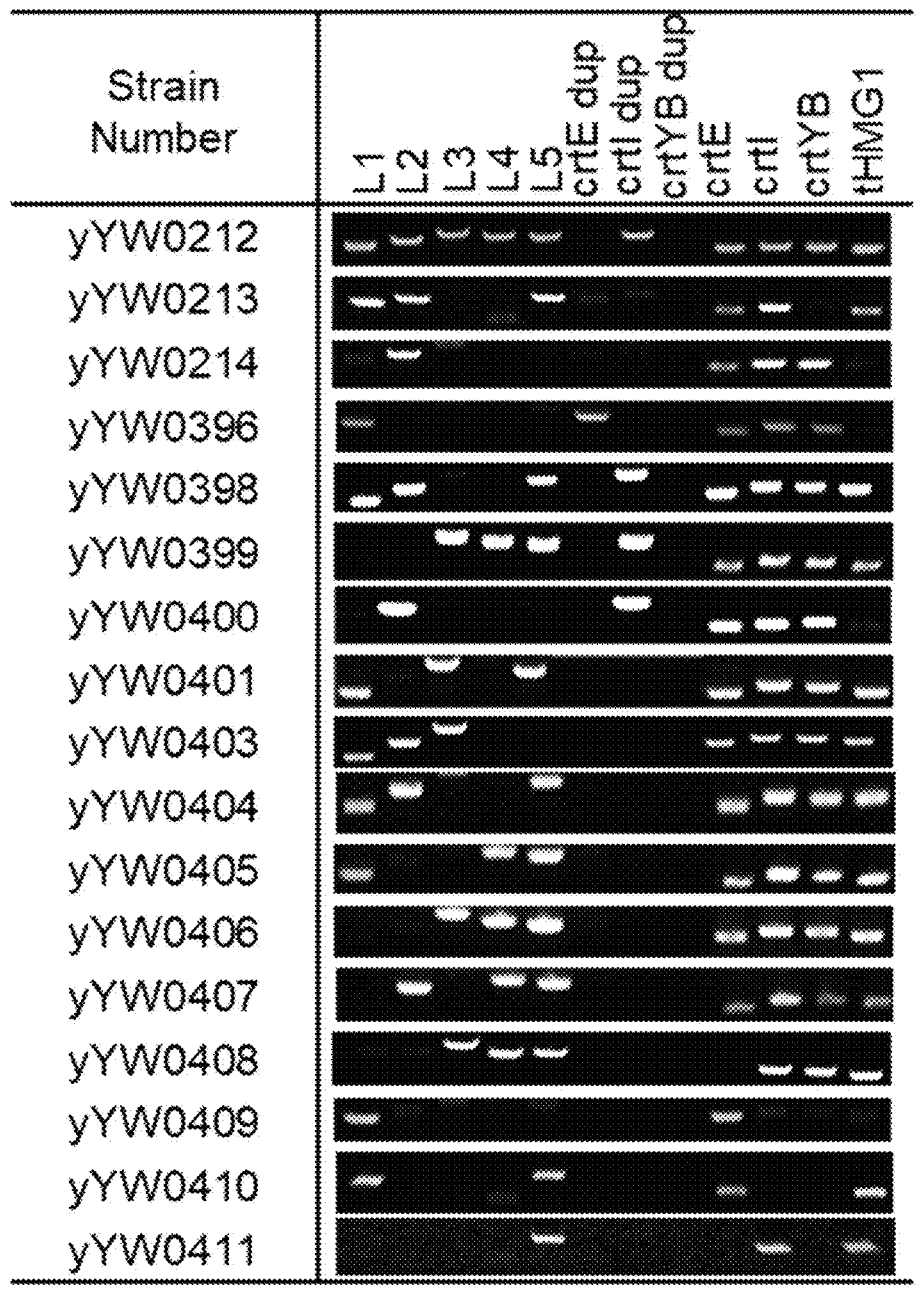
FIG. 10. PCR analysis of top-down in vitro SCRaMbLEd yeast strains. A total of 17 SCRaMbLEd pathways were analyzed by PCR with primers to test for deletion, inversion and duplication events. The template DNA for these reactions came from yeast recoveries as listed in FIG. 2. L1, L2, L3, L4, L5 are PCR reactions designed to amplify the junction regions of vector-crtE, crtE-crtI, crtI-crtYB, crtYB-tHMG1, tHMG1-vector. CrtE dup, crtI dup, crtYB dup, crtYB dup are PCR reactions designed to amplify the junction regions of duplications crtE-crtE, crtI-crtI, crtYB-crtYB. CrtE, crtI, crtYB, tHMG1 are PCR reactions designed to amplify individual genes crtE, crtI, crtYB, tHMG1.
Figure 11:
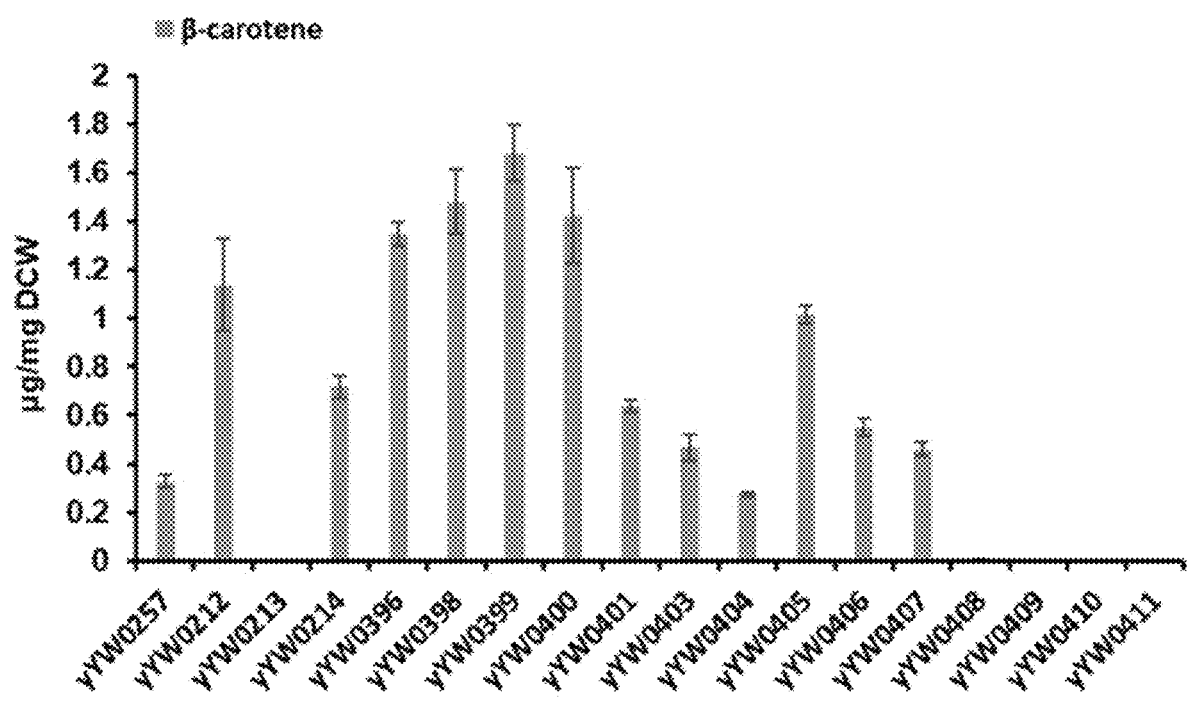
FIG. 11. HPLC measurement of β-carotene production for in vitro SCRaMbLEd strains. A total of 17 top down SCRaMbLEd strains (as listed in FIG. 2) were tested for β-carotene production. Strain yYW0257 was a control sample with nonSCRaMbLEd pLM495. Quantification was performed in biological triplicate for each strain as shown. Error bars represent standard deviation from three replicates.
Figure 12:
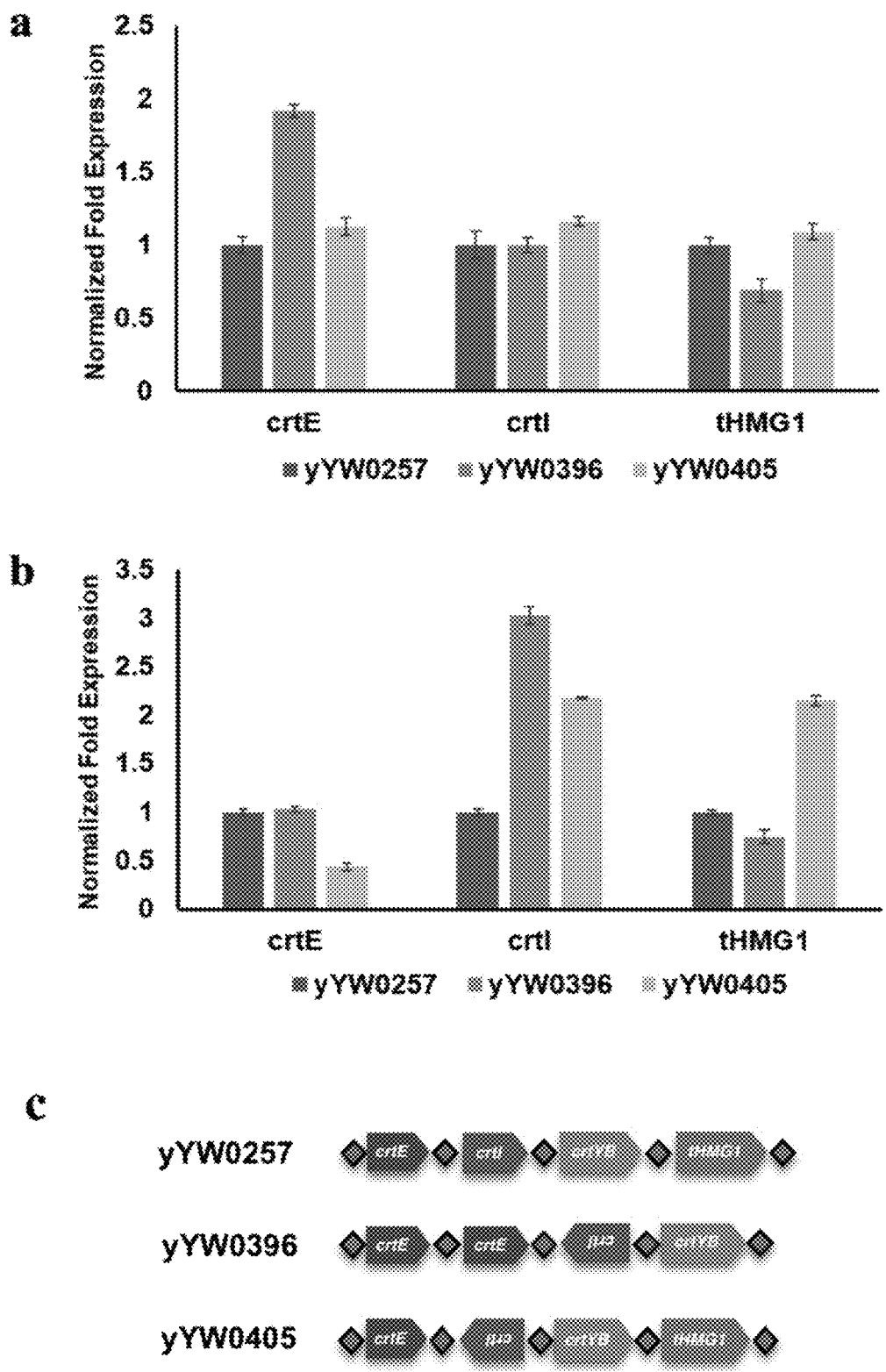
FIG. 12. qPCR analysis the inversion of crtI gene in the SCRaMbLEd pathway. (a) qPCR analysis of individual genes to assess copy number in the SCRaMbLEd construct. Purified yeast genomic DNA from strains carrying the SCRaMbLEd construct was used as template. (b) qPCR analysis to evaluate mRNA level for individual genes. Reverse transcribed cDNA from purified mRNA was used as templates. CrtYB was used as a reference gene. (c) Expected pathway structures of strains yYW0257, yYW0396, yYW0405, shown left to right for each set of three bars in panels a and b.

The SCRaMbLEd product of pLM495 was also directly transformed into S. cerevisiae for phenotypic testing. β-carotene production in yeast cells yields yellow colonies, and other pathway intermediates such as lycopene produce other colors[18]. After in vitro SCRaMbLE of pLM495, we saw various colony colors on the yeast transformation plate, including white, yellow, and deep yellow (FIG. 1f). A total of 100 yeast colonies with varied colors were picked randomly and the plasmids were recovered into E. coli for PCR analysis and DNA sequencing. Here we identified 17 unique β-carotene pathway structures that included deletion, inversion and duplication events (FIG. 2 and FIG. 10). Yeast cells carrying the 17 unique constructs were tested for β-carotene production using high-performance liquid chromatography (FIG. 2 and FIGS. 16a and 16b). The white yeast strains yYW0408, yYW0213, yYW0410, yYW0411 and yYW0409 lost production of β-carotene due to carotenoid gene deletions. The strains yYW0212, yYW0400, yYW0398 and yYW0399 increased the production of β-carotene with a 3.55.1 fold-change, likely the consequence of duplication of the crtI gene. This result is consistent with a previous report showing an additional copy of crtI in yeast leads to the production of higher levels of β-carotene[18]. Interestingly, we found that inversion of crtI in strains yYW0401, yYW0405 and yYW0396 also correlated with higher β-carotene production. We evaluated mRNA and DNA level by qPCR analysis of individual genes within the pathway in these strains (FIG. 12). The results showed increased crtI mRNA levels in the strains yYW0405 and yYW0396 and no obvious changes in the DNA level. This supports the conclusion that crtI, encoding a phytoene desaturase, catalyzes the rate-limiting step of this heterologous β-carotene pathway in *S. cerevisiae*. Of all the tested strains, yYW0399 yielded 1.7 μg per mg (dry weight) production of β-carotene, corresponding to a 5.1-fold increase in yield compared to the original construct.

Figure 13:
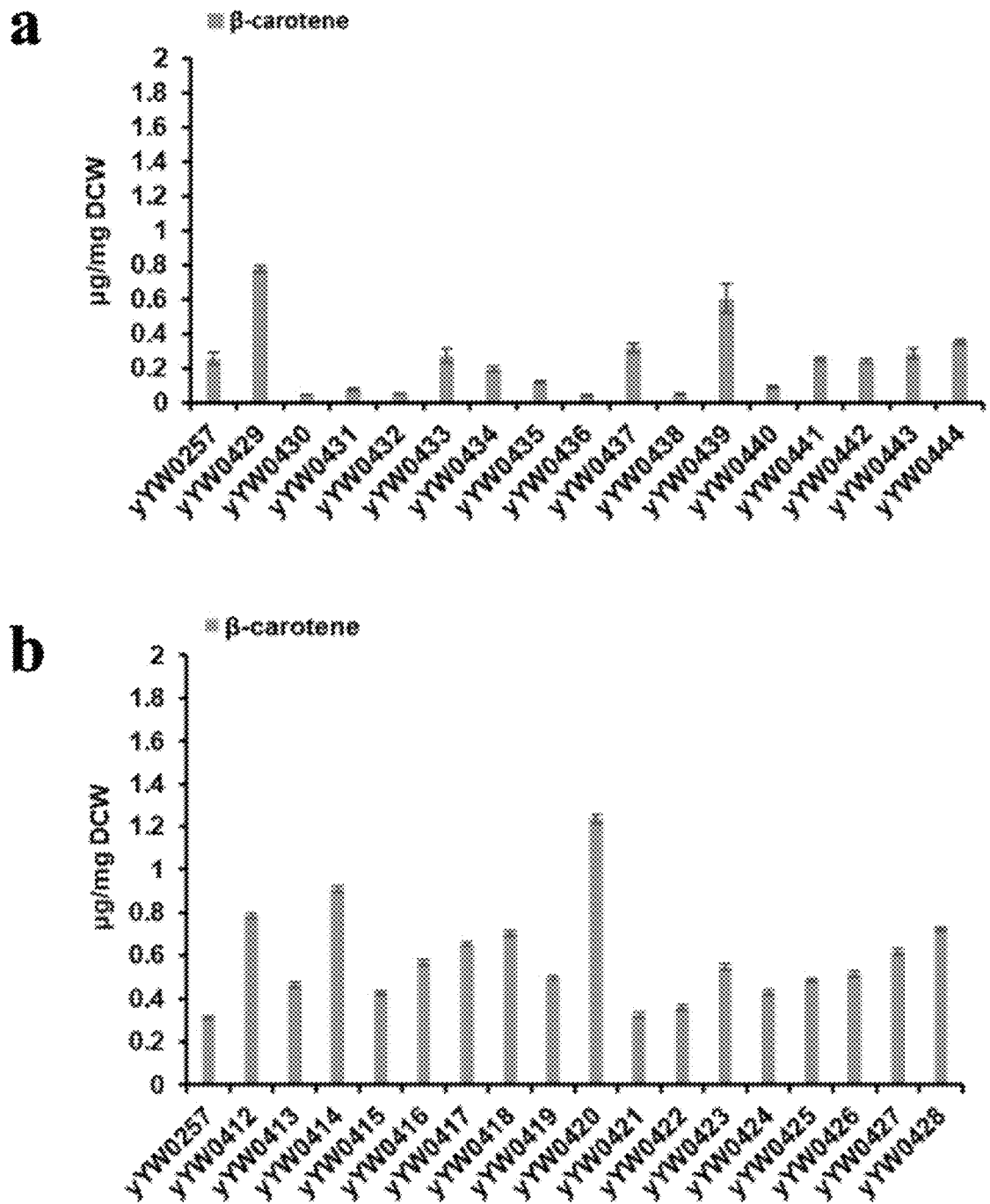
FIG. 13. HPLC measurement of β-carotene production for randomized mutation and ARTP treated strains. (a) HPLC measurement of β-carotene production of randomized mutation strains. A randomized mutation library of crtI gene in pLM495 was generated with a mutant rate at 5-10 bp/Kb. The randomized library was transformed to *S. cerevisiae* cell for phenotypic testing. A total of 16 colonies with enhanced yellow color were screened from 1611 colonies on the plate and then subjected to measure production of β-carotene. (b) HPLC measurement of β-carotene production of atmospheric and room temperature plasma (ARTP) treated strains. A total of 17 colonies with enhanced yellow color were screened from 2353 colonies following exposure of the yeast strain yYW0257 to ARTP jet for 10 and 20 s.

Distinct from traditional mutagenesis, which largely targets the base pair level, in vitro SCRaMbLE provides a simple strategy to mutagenize DNA at the level of structural variation. We compared in vitro SCRaMbLE to two conventional methods for generating libraries, random mutagenesis with error-prone PCR and atmospheric and room temperature plasma (ARTP)[21, 22]. A randomized mutation library of the crtI gene in pLM495 was generated with a mutation rate of ~5-10 bp per kb. The randomized library was transformed into *S. cerevisiae* for phenotypic testing. A total of 16 colonies with varied color were screened from 1611 colonies on the plate and then subjected to β-carotene measurements (FIG. 13a). Two strains (yYW0429 and yYW0439) showed increased production of β-carotene with 3.1 and 2.4 fold changes. Of course, these colonies are also predicted to contain ~10,000 new SNPs, any of which might be deleterious to the production of β-carotene in unanticipated ways. For ARTP, a total of 17 colonies with varied color were screened from 2353 colonies after exposing yeast strain yYW0257 to ARTP jet for 10 s and 20 s. Among these, yYW0420 showed a 3.9 fold change compared with the initial strain (FIG. 13b). For the random mutagenesis method, there were many white colored colonies generated indicating a high rate of negative mutation. For ARTP, a lot of treated cells were dead and most of the residual colonies showed unchanged color, indicating a low mutation rate. These results indicated better performance of in vitro SCRaMbLE over two other methods to improve β-carotene production.

EXAMPLE 2

Figure 3:
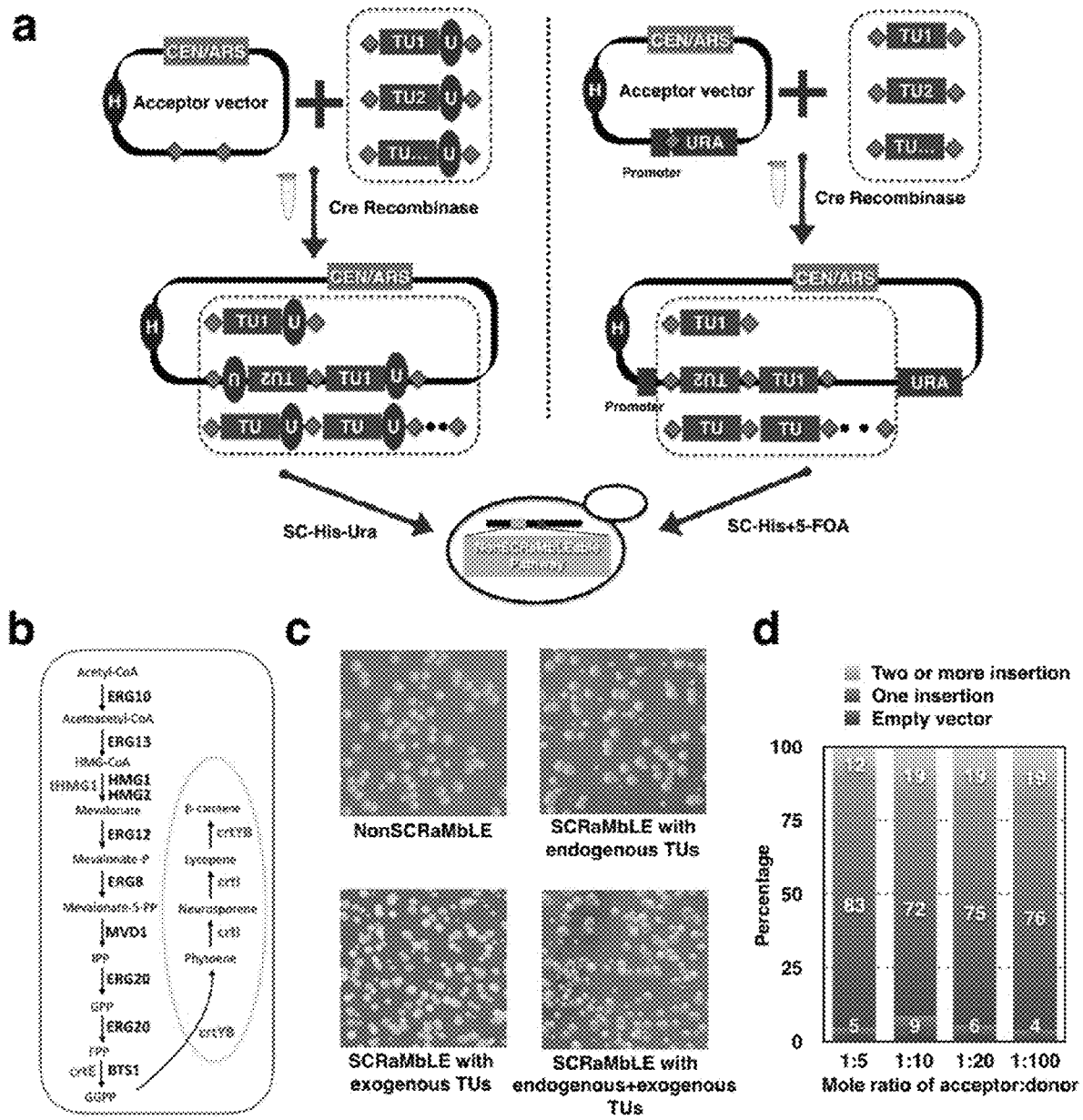
FIG. 3. Bottom-up in vitro SCRaMbLE. (a) Schematic of two independent bottom-up in vitro SCRaMbLE strategies. Left panel—donor fragments each carry a TU and a URA3 gene. The acceptor vector encodes two loxPsym sites (green diamond). Right panel—a loxPsym site is inserted in frame with the URA3 coding sequence (FIG. 14). Donor fragments are flanked by loxPsym sites. In both cases, the acceptor vector and the pool of donor TUs constructs are mixed with Cre recombinase in vitro. The donor TUs may be randomly inserted into loxPsym sites of the acceptor vector. Note that in bottom-up SCRaMbLE the core β-carotene pathway itself is not in a SCRaMbLE format (i.e. unlike "top down", there are no lox sites flanking core pathway genes). (yellow box "NonSCRaMbLEable pathway" integrated into genome). Transcription unit (TU), HIS3 auxotroph marker (H), URA3 auxotroph marker (U). (b) Overview of the carotenoid biosynthetic pathway in S. cerevisiae. Genes shown in black (those not designated as red) are endogenous to S. cerevisiae. Genes shown in red (tHMG1, crtE, crtYB, crtI), are non-native, and derive from X. dendrorhous (crtE, crtYB, crtI), and one from S. cerevisiae (truncated 3-hydroxy-3-methylglutaryl-coenzyme A reductase gene [tHMG1]). (c) Yeast colonies transformed with bottom-up in vitro SCRaMbLEd candidate carotenogenic TU pools. The non-SCRaMbLE sample was transformed with the acceptor vector as a control. Three other in vitro SCRaMbLEd pools consisted of endogenous TUs, exogenous TUs, and endogenous+exogenous TUs as indicated. (d) The efficiency of bottom-up in vitro SCRaMbLE (strategy 1). Different mole ratios of acceptor vector with donor TUs (1:5, 1:10, 1:20, 1:100) were used to test SCRaMbLE efficiency. pYW0113 was used as the acceptor vector; crtI TU and tHMG1 TU were used as donor fragments. A total of 100 yeast colonies for each group were tested using long fragment PCR and restriction enzyme digestion of recovered plasmids.
Figure 14:
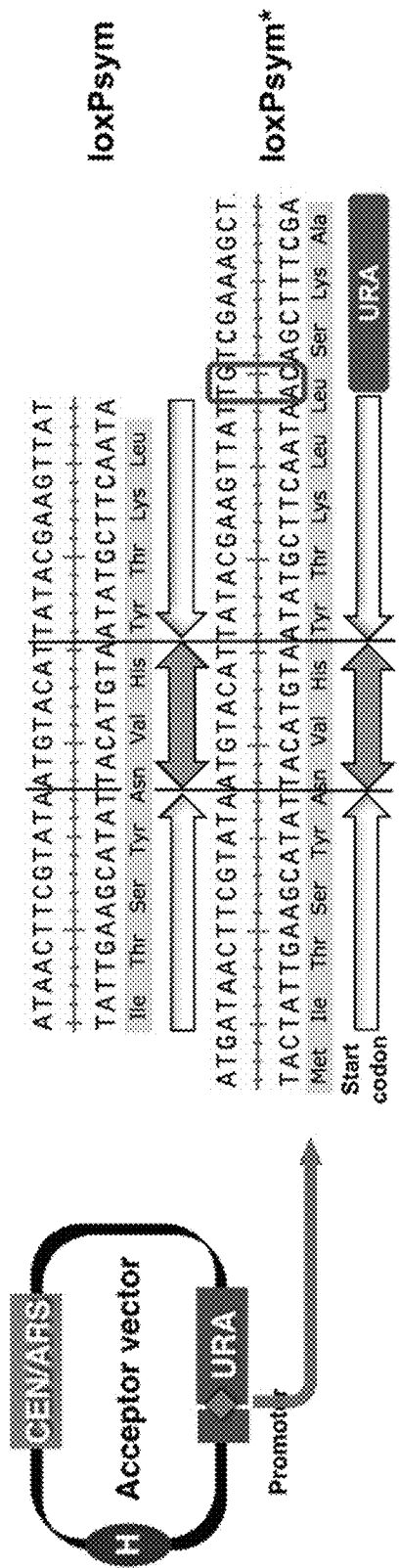
FIG. 14. Bottom-up of in vitro SCRaMbLE with redesigned loxPsym site. Structure and sequence comparison between loxPsym* and loxPsym. The redesigned loxPsym site (loxPsym*) is 36 bp and the insertion after start codon have no impact on the expression of URA3. The sequence of the loxPsym top DNA strand is SEQ ID NO:1. The sequence of the loxPsym bottom DNA strand is SEQ ID NO:2. The sequence of the loxP top DNA strand is SEQ ID NO:3. The sequence of the loxP bottom DNA strand is SEQ ID NO:4. The sequence of the loxPsym* top DNA strand is SEQ ID NO:5. The sequence of the loxPsym* bottom DNA strand is SEQ ID NO:6. The amino acid sequence below the loxPsym DNA sequence is SEQ ID NO:7. The amino acid sequence below the loxPsym* DNA sequence is SEQ ID NO:8.

Bottom-Up In Vitro SCRaMbLE: SCRaMbLEing Transcription Units for Pathway Augmentation "Bottom-up" in vitro SCRaMbLE starts with a centromeric acceptor vector and a series of "donor fragments"; the basic goal here is to evaluate a series of candidate genes (represented as "donor fragments") for their ability to boost production of the core pathway (resident in the chromosome in a non-SCRaMbLEable format) (FIG. 3a). The donor fragments can consist of the main pathway genes themselves, other genes from the host that produce starting metabolites, or any candidate gene that may positively impact pathway flux. There are two ways to use the bottom-up system based on how the selectable markers are exploited. In the first version (left panel, FIG. 3a), the acceptor vector has two loxPsym sites. The donor fragments are generated from a universal vector, which is an *E. coli*-based plasmid enabled for yeast Golden Gate assembly and red/white *E. coli* colony screening[23]. The donor fragments each encode a URA3 gene as a positively selectable marker; yeast transformants that are His+ Ura+ are guaranteed to have picked up at least one donor fragment during the in vitro recombination reaction. In the second version, (right panel, FIG. 3a), the acceptor vector encodes a single loxPsym site, inserted in the URA3 coding sequence by adding 2 base pairs (TG) to the 3' end of the 34 bp loxPsym site, resulting in an in-frame insertion of 36 bp (FIG. 14). A functional Ura3 protein is produced, enabling selection on medium lacking uracil for the parental vector. Recombination of one or more donor fragments into this site physically separates the URA3 promoter and ATG codon from the coding sequence, enabling negative selection on 5-fluoroorotic acid (5-FOA) medium[24]. Here the donor fragments can be directly amplified by PCR with primers encoding terminal loxPsym sites. The bottom-up in vitro SCRaMbLE reaction consists of a pool of donor fragments, the acceptor vector, and Cre recombinase. The donor fragments can be heterologous or endogenous transcription units. When the in vitro SCRaMbLEd pool of DNA molecules is transformed to an appropriately engineered host strain with a resident "unSCRaMbLEable" pathway, the addition of one or more candidate TUs will add new genes, and those that augment pathway production can be selected by looking for enhanced color.

Using the β-carotene pathway as an example, we first converted the pathway genes (crtI, crtE and crtYB) to the unSCRaMbLEable format (no lox sites) and integrated them into the CAN1 locus (FIG. 3b). We generated 7 candidate donor TUs fragments from the mevalonate pathway (ERG10, ERG13, ERG12, ERGS, MVD1, ERG20 and BTS1) and 4 candidate donor TUs fragments from the exogenous pathway (crtI crtE, crtYB, and tHMG1) as candidates for bottom-up SCRaMbLE. Using the strategy in the left panel of FIG. 3a, three SCRaMbLEd TU pools (endogenous TUs, exogenous TUs, and all TUs) were transformed into a yeast strain yYW0301 encoding the resident, unSCRaMbLEable β-carotene pathway. After incubation for 3 days at 30° C., brighter yellow to orange colonies grew only on selective plates carrying SCRaMbLEd exogenous TU pools. There were no distinct color variants on plates with the SCRaMbLEd endogenous TU pool (FIG. 3c), suggesting that varying the copy number of genes in the endogenous mevalonate pathway has no major impact on β-carotene pathway productivity, based on visual inspection.

Figure 15:
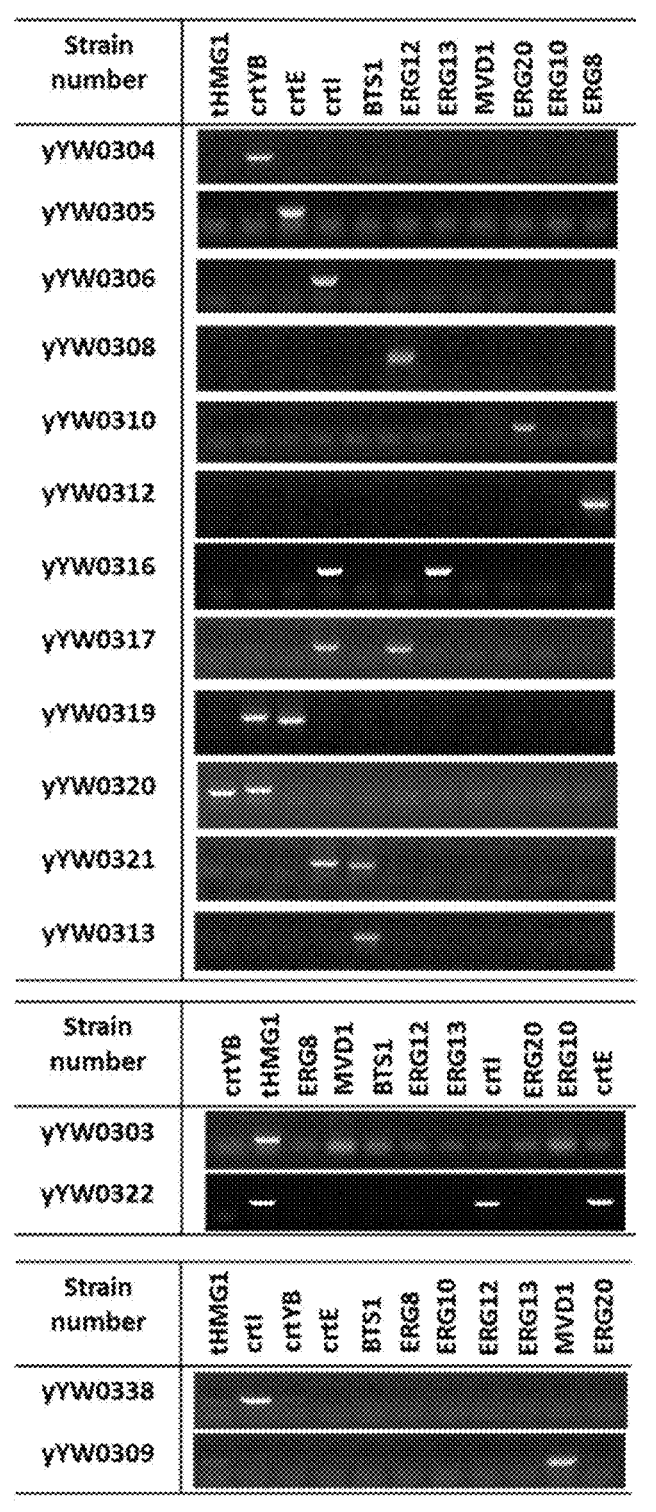

To test the insertion efficiency for the first version of bottom-up SCRaMbLE, we performed the in vitro Cre reaction with different ratios of acceptor vector and donor fragments. Reaction products were evaluated after transformation into yeast. Most of the SCRaMbLEd yeast strains (70%-85%) carried a single insertion. Increasing the donor fragment: acceptor vector ratio by ten-fold nearly doubled the number of times we observed two or more insertion events, from 12% to ~20% (FIG. 3d). In fact, we were able to assemble the entire 4-gene beta carotene pathway in a single bottom up in vitro SCRaMbLE experiment using this strategy (FIG. 15).

Figure 16:
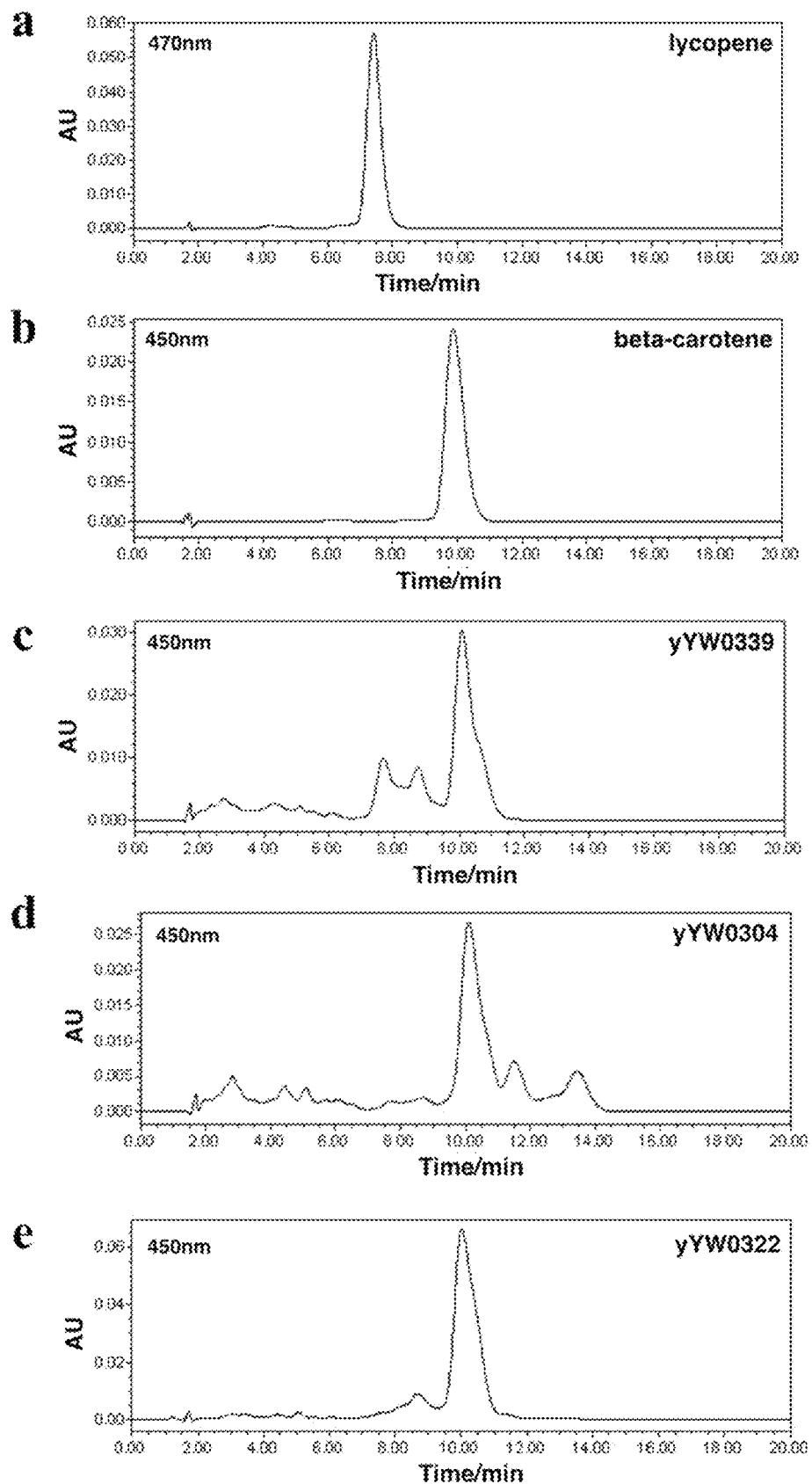
FIG. 16. HPLC profiles for bottom-up SCRaMbLEd yeast strains. (a,b) HPLC profile of standards, purified lycopene and beta-carotene; (c) HPLC curve of strain yYW0339. yYW0339 is the initial strain with non-SCRaMbLEable pathway integrated at CAN1; (d) HPLC curve of strain yYW0304. yYW0304 carries a SCRaMbLEd construct with an additional crtYB gene inserted. Two unknown peaks appear after the of β-carotene peak. (e) HPLC curve of strain yYW0322. yYW0322 carries a SCRaMbLEd construct with additional copies of three genes crtI, crtE and tHMG1 and produces increased levels of β-carotene with minimal non-specific peaks. AU, absorbance unit.

Single colonies of diverse colors and intensity were randomly streaked out to interrogate the inheritance of color formation. After yeast colony PCR analysis with TU specific primers in 100 randomly picked colonies, 17 strains showed diverse SCRaMbLEd structures (FIG. 16). To verify colony color was dependent on SCRaMbLEd plasmids, the yeast plasmids were recovered into *E. coli* and then re-transformed into the parental yeast strain yYW0246. All re-transformed strains developed the identical colony color compared with original SCRaMbLEd isolates (FIG. 4a).

Figure 4:
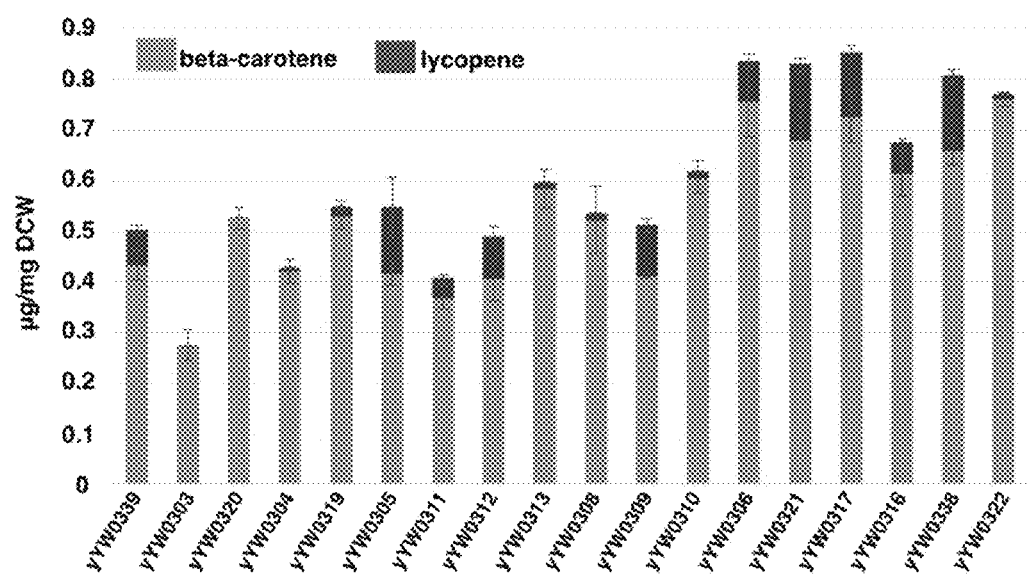
FIG. 4. Bottom-up in vitro SCRaMbLE for β-carotene pathway optimization. (a) Phenotype-genotype correlation of the β-carotene pathway after bottom-up in vitro SCRaMbLE (strategy 1). A total of 17 SCRaMbLEd yeast strains were isolated for testing colony color and determination of SCRaMbLEd construct sequences. The pictures of yeast color for both SCRaMbLEd strains and strains with re-introduced SCRaMbLEd plasmid were taken after 3 days incubation at 30° C. on SC-Ura medium. The SCRaMbLEd pathway structure was initially analyzed by restriction enzyme digestion to check the number of insertions and PCR analysis to evaluate which genes were inserted. Primer walking sequencing was applied to verify the sequence of all recovered plasmids. yYW0339 with only a LIRAS gene inserted was used as a control strain. (b) HPLC measurement of carotenoid production for SCRaMbLEd yeast strains. Quantification was performed in biological triplicate for each strain as shown. Error bars represent standard deviation from three replicates.

Yeast colonies with diverse pathway structure were analyzed for production of β-carotene and lycopene, determined by high-performance liquid chromatography (FIG. 4b).

Figure 17:
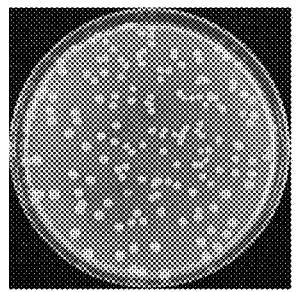
FIG. 17. Stability of bottom-up in vitro SCRaMbLEd constructs carrying two and three selection markers. After continuous passage for 100 generations with SCRaMbLEd strains yYW0322 and yYW0320, the recombination ratio is 1/159 for strain yYW0322 and 5/120 for strain yYW0320. The recombination events occurred between two URA3 genes based on sequence analysis.
Figure 17:
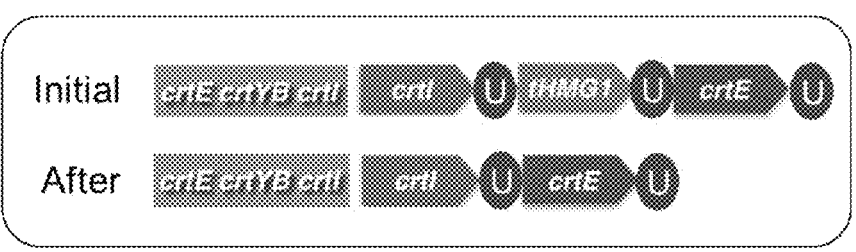
Figure 17:
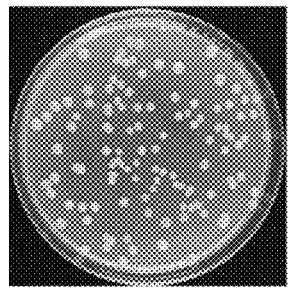
Figure 17:
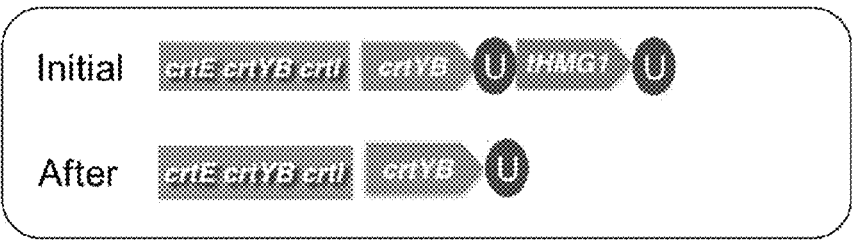

Phenotype-genotype correlation of β-carotene pathway indicated that an additional copy of crtI gene led to a deep orange colony color and increased production of β-carotene (compare strains yYW0306 with yYW0339). On the other hand, strain yYW0338 with two additional copies of the crtI gene did not increase production of β-carotene beyond that observed in yYW0306, indicating one additional copy of crtI is sufficient to optimize the β-carotene pathway. An additional copy of tHMG1 can make the colony color bright yellow (yYW0303, yYW0320, yYW0322) and produces an HPLC profile very similar to that of purified β-carotene (FIG. 17). Interestingly, an additional copy of crtYB can make the colony color deep yellow (yYW0304, yYW0319) but in this case two unknown peaks appeared after the peak of β-carotene, which are presumably caused by production of other carotenoids[19]. (FIG. 17).

Figure 18:
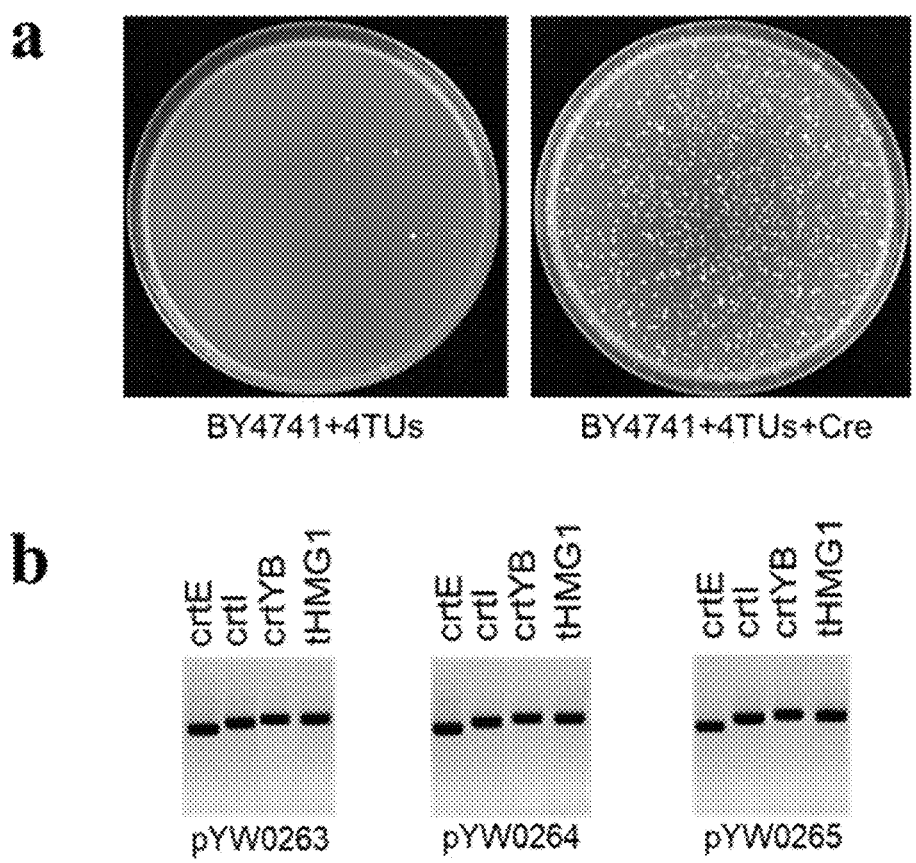
FIG. 18. Using bottom-up in vitro SCRaMbLE to assemble the entire β-carotene pathway from exogenous TUs. (a) BY4741, a wild-type yeast strain not carrying an integrated copy of the β-carotene pathway, was transformed with bottom-up in vitro SCRaMbLEd carotenogenic TU pools using strategy of the first version (left panel, FIG. 3a). Yellow colored colonies were observed on the plate. (b) PCR analysis of colored yeast colonies. The template DNA used are plasmids recovered from three colored yeast colonies. Approximately 4 percent of yeast colonies are yellow in color, suggesting bottom-up in vitro SCRaMbLE assembly of all four components of the Crt pathway.

In the first version of bottom-up SCRaMbLE, because each donor fragment encodes a URA3 gene, it can lead to instability in constructs with multiple TUs incorporated. We performed an experiment to test the stability of in vitro SCRaMbLEd constructs carrying two and three TUs, yeast strains yYW0320 and yYW0322 respectively. After continuous passage for 100 generations, we identified instances of recombination, 1/159 for yYW0322 and 5/120 for yYW0320 (FIG. 18). This is obviously undesirable for any kind of production application. This problem is circumvented with the second version of bottom-up in vitro SCRaMbLE (FIG. 3a, right panel), which yields recombined products lacking direct repeats and additionally enables counter-selection to remove background unmodified acceptor vector.

EXAMPLE 3

Materials and Methods used to obtain results presented in this disclosure.

Strains and Plasmids are Described in Table 1 and 2.

Construction of loxPsym Site Plasmids

The pathway encoded in pLM495 was initially assembled using VEGAS (versatile genetic assembly system)[19], and loxPsym sites were subsequently introduced between each pathway gene through PCR reactions using primers that introduced loxPsym sites and terminal, inward pointing BsaI sites. pLM495 was then assembled by Golden Gate. The ~100 kb synIXR-BAC was previously described[14]. pYW0261 was assembled from 500 bp sectional sequences randomly chosen from β-carotene pathway genes (BTS1, crtE, crtI, crtYB, ERG8, ERG10, ERG12, ERG13, ERG20), respectively and interspersed with loxPsym sites.

Construction of Acceptor Vector and Donor Fragments

Acceptor vector pYW0113 is a yeast centromere plasmid with a HIS3 gene as auxotrophic marker and a red fluorescent protein (RFP) gene flanked by two loxPsym sites. Donor universal vector pYW0120 was assembled using stepwise polymerase chain reaction (PCR) to introduce "NotI-loxPsym-BsaI-RFP-BsAI-URA-loxPsym-NotI" structure to a high copy E. coli plasmid backbone. The donor transcription units were amplified with primers that introduced terminal BsaI restriction sites, which were subsequently assembled into the universal vector pYW0120 by Golden Gate assembly. All donor fragments "TU+URA" were obtained by NotI digestion followed by gel purification.

synIXR-BAC Isolation synIXR-BAC DNA was prepared using alkaline lysis and ethanol precipitation as previously described[32].

In Vitro SCRaMbLE

The Cre recombinase reaction was set up as per the manufacturer's instructions (NEB, M0298L) and incubated at 37° C. for 1 h. The Cre enzyme was heat inactivated for 10 minutes at 70° C. For top-down in vitro SCRaMbLE, 100 ng of DNA was added in a total reaction volume of 10 μl with 1 μl of Cre recombinase. For bottom-up in vitro SCRaMbLE, 200 ng acceptor vector was mixed with the donor fragments pool (1000 ng in total) in a reaction volume of 50 μl with 1 μl of high concentration Cre recombinase (NEB, M0298M). Both SCRaMbLEd pools were transformed to hosts for genotype and phenotype testing. For bottom-up in vitro SCRaMbLE, SC-Ura-His medium or SC-His+5-FOA medium are used to select for recombined constructs, depending whether the first or second version is used.

Yeast Plasmid Recovery

SCRaMbLEd plasmids were recovered from yeast using the following method. A volume of 1.5 ml overnight cultured yeast cells were collected and resuspended in 250 μl of P1 (Qiagen) with 10 mg per ml RNase and 200 μl glass beads followed by shaking for 10 mins to mechanically break open the cells. Then plasmids were isolated using with the standard alkaline lysis and a Qiagen miniprep spin column to isolate the DNA. The plasmids were eluted with 30 μl of elution buffer. 15 μl of the elution was transformed to 100 μl of E. coli competent cells.

Plasmid Structure Determination

Methods to analyze recovered plasmids included restriction digestion analysis, PCR analysis with gene specific primers, Sanger sequencing and PacBio sequencing. The top-down SCRaMbLEd plasmid pYW0108 with duplicated genes was initially analyzed using restriction digestion and then sent for PacBio sequencing. Other top-down SCRaMbLEd plasmids were initially analyzed using restriction digestion and subsequently analyzed using a primer walking sequencing method. All bottom-up SCRaMbLEd plasmids were initially analyzed by restriction digestion to check the number of insertions and PCR analysis to identify the inserted gene. Primer walking sequencing was applied to verify all the recovered bottom-up SCRaMbLEd plasmids.

ARTP (Atmospheric and Room Temperature Plasma) of Yeast Strains

The yeast strain yYW0257 with $OD_{600}$ value at 2 was selected to undergo ARTP. The RF power input was set to 120 W and the temperature of the plasma jet was set to 25-35° C. 10 μl of the cell culture was dipped onto the stainless steel minidisc and then exposed to ARTP jet for 0 s (control), 10 s, 20 s, 30 s respectively. Then the treated yeast cells were diluted in the selective medium. This was done on ARTP-II device from Wuxi Research Institute of Applied Technologies (Wuxi, China).

PacBio Sequencing of SCRaMbLEd Library

The analyzed library was derived from a DNA pool of in vitro SCRaMbLEd pLM495 by linearizing with NotI and SalI. The library was sequenced on an RSII sequencer from Pacific Biosystems (Menlo Park, Calif., USA). The alignment was performed with software BLAST.

HPLC Measurement of Carotenoid Production

SCRaMbLEd yeast strains and control yeast strains were cultured in 5 ml of SC-Ura liquid medium at 250 rpm, 30° C. in a shaking incubator. The saturated cultures were diluted to an initial $OD_{600}$ of 0.1 in 50 ml of SC-Ura liquid medium and grown for 48 h with the same condition. An aliquot of the culture was centrifuged for 5 min at 4000 g. Cells were resuspended in 1 ml of 3M HCl. The resuspended cells were heated in a boiled water bath for 3 min, and then cooled in an ice-bath for 3 min, repeating twice. Cell pellets were then washed twice with double-distilled water and harvested by centrifugation. After removal of the supernatant, the cells were resuspended in 1 ml acetone and vortexed for 10 min. The acetone extracts were centrifuged and filtered with a 0.22 μm filter for subsequent analysis. A portion of each sample was harvested and dried at 70° C. for measurement of the dry cell weight. The analysis of carotenoids was performed by HPLC (Waters 2695) equipped with SUPELCO C18 column (33 cm×4.6 mm) and UV detection at 450 nm and 470 nm. The mobile phase consisted of acetonitrile-methanol-dichloromethane (18:90:2 v/v/v) with a flow rate of 0.3 mL per min at 25° C. The content of the carotenoids was expressed as μg per mg dry cell weight (μg per mg DCW). Each of the samples were performed on technical triplicates.

TABLE 1

Yeast strains used in this study.

| Strain name | Description | Genotype |
|---|---|---|
| BY4741 | | MATa his3Δ1 leu2Δ0 met15Δ0 ura3Δ0 |
| yYW0257 | Top-down in vitro SCRaMbLE control strain with unSCRaMbLEd pLM495 | MATa his3Δ1 leu2Δ0 met15Δ0 ura3Δ0 |
| yYW0212 | Top-down in vitro SCRaMbLEd pLM495 yeast strain (crtI duplication) | MATa his3Δ1 leu2Δ0 met15Δ0 ura3Δ0 |
| yYW0213 | Top-down in vitro SCRaMbLEd pLM495 yeast strain (crtYB deletion) | MATa his3Δ1 leu2Δ0 met15Δ0 ura3Δ0 |
| yYW0214 | Top-down in vitro SCRaMbLEd pLM495 yeast strain (crtI inversion, crtE inversion, tHMG1 deletion) | MATa his3Δ1 leu2Δ0 met15Δ0 ura3Δ0 |
| yYW0396 | Top-down in vitro SCRaMbLEd pLM495 yeast strain (crtE duplication, crtI inversion, tHMG1 deletion) | MATa his3Δ1 leu2Δ0 met15Δ0 ura3Δ0 |
| yYW0398 | Top-down in vitro SCRaMbLEd pLM495 yeast strain (crtI duplication, crtYB inversion) | MATa his3Δ1 leu2Δ0 met15Δ0 ura3Δ0 |
| yYW0399 | Top-down in vitro SCRaMbLEd pLM495 yeast strain (crtE inversion, crtI duplication) | MATa his3Δ1 leu2Δ0 met15Δ0 ura3Δ0 |
| yYW0400 | Top-down in vitro SCRaMbLEd pLM495 yeast strain (crtI duplication, two crtI and crtE inversion, tHMG1 deletion) | MATa his3Δ1 leu2Δ0 met15Δ0 ura3Δ0 |
| yYW0401 | Top-down in vitro SCRaMbLEd pLM495 yeast strain (crtI and crtYB inversion) | MATa his3Δ1 leu2Δ0 met15Δ0 ura3Δ0 |
| yYW0403 | Top-down in vitro SCRaMbLEd pLM495 yeast strain (tHMG1 inversion) | MATa his3Δ1 leu2Δ0 met15Δ0 ura3Δ0 |
| yYW0404 | Top-down in vitro SCRaMbLEd pLM495yeast strain (crtYB inversion) | MATa his3Δ1 leu2Δ0 met15Δ0 ura3Δ0 |
| yYW0405 | Top-down in vitro SCRaMbLEd pLM495 yeast strain (crtI inversion) | MATa his3Δ1 leu2Δ0 met15Δ0 ura3Δ0 |
| yYW0406 | Top-down in vitro SCRaMbLEd pLM495 yeast strain (crtE inversion) | MATa his3Δ1 leu2Δ0 met15Δ0 ura3Δ0 |
| yYW0407 | Top-down in vitro SCRaMbLEd pLM495 yeast strain (crtE and crtI inversion) | MATa his3Δ1 leu2Δ0 met15Δ0 ura3Δ0 |
| yYW0408 | Top-down in vitro SCRaMbLEd pLM495 yeast strain (crtE deletion) | MATa his3Δ1 leu2Δ0 met15Δ0 ura3Δ0 |
| yYW0409 | Top-down in vitro SCRaMbLEd pLM495 yeast strain (crtI crtYB and tHMG1 deletion) | MATa his3Δ1 leu2Δ0 met15Δ0 ura3Δ0 |
| yYW0410 | Top-down in vitro SCRaMbLEd pLM495 yeast strain (crtI and crtYB deletion) | MATa his3Δ1 leu2Δ0 met15Δ0 ura3Δ0 |
| yYW0411 | Top-down in vitro SCRaMbLEd pLM495 yeast strain (crtE and crtI deletion) | MATa his3Δ1 leu2Δ0 met15Δ0 ura3Δ0 |
| yYW0301 | BY4741 with β-carotene gene crtYB, crtI, crtE at CAN1 | MATa his3Δ1 leu2Δ0 met15Δ0 ura3Δ0 CAN1::crtI-crtYB-crtE-LEU |
| yYW0339 | Bottom-up in vitro SCRaMbLE control | MATa his3Δ1 leu2Δ0 met15Δ0 ura3Δ0 CAN1::crtI-crtYB-crtE-LEU |
| yYW0303 | Bottom-up in vitro SCRaMbLEd plasmid pYW0113 with tHMG1 inserted | MATa his3Δ1 leu2Δ0 met15Δ0 ura3Δ0 CAN1::crtI-crtYB-crtE-LEU |
| yYW0304 | Bottom-up in vitro SCRaMbLEd plasmid pYW0113 with crtYB inserted | MATa his3Δ1 leu2Δ0 met15Δ0 ura3Δ0 CAN1::crtI-crtYB-crtE-LEU |
| yYW0305 | Bottom-up in vitro SCRaMbLEd plasmid pYW0113 with crtE inserted | MATa his3Δ1 leu2Δ0 met15Δ0 ura3Δ0 CAN1::crtI-crtYB-crtE-LEU |
| yYW0306 | Bottom-up in vitro SCRaMbLEd plasmid pYW0113 with crtI inserted | MATa his3Δ1 leu2Δ0 met15Δ0 ura3Δ0 CAN1::crtI-crtYB-crtE-LEU |
| yYW0308 | Bottom-up in vitro SCRaMbLEd plasmid pYW0113 with ERG12 inserted | MATa his3Δ1 leu2Δ0 met15Δ0 ura3Δ0 CAN1::crtI-crtYB-crtE-LEU |
| yYW0309 | Bottom-up in vitro SCRaMbLEd plasmid pYW0113 with MVD1 inserted | MATa his3Δ1 leu2Δ0 met15Δ0 ura3Δ0 CAN1::crtI-crtYB-crtE-LEU |
| yYW0310 | Bottom-up in vitro SCRaMbLEd plasmid pYW0113 with ERG20 inserted | MATa his3Δ1 leu2Δ0 met15Δ0 ura3Δ0 CAN1::crtI-crtYB-crtE-LEU |
| yYW0311 | Bottom-up in vitro SCRaMbLEd plasmid pYW0113 with ERG10 inserted | MATa his3Δ1 leu2Δ0 met15Δ0 ura3Δ0 CAN1::crtI-crtYB-crtE-LEU |

TABLE 1-continued

Yeast strains used in this study.

| Strain name | Description | Genotype |
|---|---|---|
| yYW0312 | Bottom-up in vitro SCRaMbLEd plasmid pYW0113 with ERG8 inserted | MATa his3Δ1 leu2Δ0 met15Δ0 ura3Δ0 CAN1::crtI-crtYB-crtE-LEU |
| yYW0313 | Bottom-up in vitro SCRaMbLEd plasmid pYW0113 with BTS1 inserted | MATa his3Δ1 leu2Δ0 met15Δ0 ura3Δ0 CAN1::crtI-crtYB-crtE-LEU |
| yYW0316 | Bottom-up in vitro SCRaMbLEd plasmid pYW0113 with crtI, ERG13 inserted | MATa his3Δ1 leu2Δ0 met15Δ0 ura3Δ0 CAN1::crtI-crtYB-crtE-LEU |
| yYW0317 | Bottom-up in vitro SCRaMbLEd plasmid pYW0113 with crtI, ERG12 inserted | MATa his3Δ1 leu2Δ0 met15Δ0 ura3Δ0 CAN1::crtI-crtYB-crtE-LEU |
| yYW0319 | Bottom-up in vitro SCRaMbLEd plasmid pYW0113 with crtYB, crtE inserted | MATa his3Δ1 leu2Δ0 met15Δ0 ura3Δ0 CAN1::crtI-crtYB-crtE-LEU |
| yYW0320 | Bottom-up in vitro SCRaMbLEd plasmid pYW0113 with crtYB, tHMG1 inserted | MATa his3Δ1 leu2Δ0 met15Δ0 ura3Δ0 CAN1::crtI-crtYB-crtE-LEU |
| yYW0321 | Bottom-up in vitro SCRaMbLEd plasmid pYW0113 with crtI, BTS1 inserted | MATa his3Δ1 leu2Δ0 met15Δ0 ura3Δ0 CAN1::crtI-crtYB-crtE-LEU |
| yYW0322 | Bottom-up in vitro SCRaMbLEd plasmid pYW0113 with crtE, crtI, and tHMG1 inserted | MATa his3Δ1 leu2Δ0 met15Δ0 ura3Δ0 CAN1::crtI-crtYB-crtE-LEU |
| yYW0338 | Bottom-up in vitro SCRaMbLEd plasmid pYW0113 with two crtI inserted | MATa his3Δ1 leu2Δ0 met15Δ0 ura3Δ0 CAN1::crtI-crtYB-crtE-LEU |
| yYW0412 | ARTP for yYW0257 | MATa his3Δ1 leu2Δ0 met15Δ0 ura3Δ0 |
| yYW0413 | ARTP for yYW0257 | MATa his3Δ1 leu2Δ0 met15Δ0 ura3Δ0 |
| yYW0414 | ARTP for yYW0257 | MATa his3Δ1 leu2Δ0 met15Δ0 ura3Δ0 |
| yYW0415 | ARTP for yYW0257 | MATa his3Δ1 leu2Δ0 met15Δ0 ura3Δ0 |
| yYW0416 | ARTP for yYW0257 | MATa his3Δ1 leu2Δ0 met15Δ0 ura3Δ0 |
| yYW0417 | ARTP for yYW0257 | MATa his3Δ1 leu2Δ0 met15Δ0 ura3Δ0 |
| yYW0418 | ARTP for yYW0257 | MATa his3Δ1 leu2Δ0 met15Δ0 ura3Δ0 |
| yYW0419 | ARTP for yYW0257 | MATa his3Δ1 leu2Δ0 met15Δ0 ura3Δ0 |
| yYW0420 | ARTP for yYW0257 | MATa his3Δ1 leu2Δ0 met15Δ0 ura3Δ0 |
| yYW0421 | ARTP for yYW0257 | MATa his3Δ1 leu2Δ0 met15Δ0 ura3Δ0 |
| yYW0422 | ARTP for yYW0257 | MATa his3Δ1 leu2Δ0 met15Δ0 ura3Δ0 |
| yYW0423 | ARTP for yYW0257 | MATa his3Δ1 leu2Δ0 met15Δ0 ura3Δ0 |
| yYW0424 | ARTP for yYW0257 | MATa his3Δ1 leu2Δ0 met15Δ0 ura3Δ0 |
| yYW0425 | ARTP for yYW0257 | MATa his3Δ1 leu2Δ0 met15Δ0 ura3Δ0 |
| yYW0426 | ARTP for yYW0257 | MATa his3Δ1 leu2Δ0 met15Δ0 ura3Δ0 |
| yYW0427 | ARTP for yYW0257 | MATa his3Δ1 leu2Δ0 met15Δ0 ura3Δ0 |
| yYW0428 | ARTP for yYW0257 | MATa his3Δ1 leu2Δ0 met15Δ0 ura3Δ0 |
| yYW0429 | Random Mutation for pLM495 of gene crtI (S[AGC]339S[AGU], E[GAG]368E[GAA]) | MATa his3Δ1 leu2Δ0 met15Δ0 ura3Δ0 |
| yYW0430 | Random Mutation for pLM495 of gene crtI (K[AAA]9I[AUA], C[UGU]182F[UUU]) | MATa his3Δ1 leu2Δ0 met15Δ0 ura3Δ0 |
| yYW0431 | Random Mutation for pLM495 of gene crtI (L[CUC]66L[CUA], D[GAU]69D[UAU]) | MATa his3Δ1 leu2Δ0 met15Δ0 ura3Δ0 |
| yYW0432 | Random Mutation for pLM495 of gene crtI (P[CCU]154S[UCU], A[GCC]265V[GUC], D[GAC]267D[GAU], S[UCC]295S[UCG], Q[CAA]309H[CAU], S[AGC]339C[GGC]) | MATa his3Δ1 leu2Δ0 met15Δ0 ura3Δ0 |
| yYW0433 | Random Mutation for pLM495 of gene crtI (N[AAC]41N[AAU], G[GGC]155G[GGU], I[AUC]241I[AUU], A[GCC]373V[GUC]) | MATa his3Δ1 leu2Δ0 met15Δ0 ura3Δ0 |
| yYW0434 | Random Mutation for pLM495 of gene crtI (K[AAG]243D[AAC], V[GUU]322I[AUU], G[GGU]323A[GCU], I[AUC]352I[AUU], R[CGA]384R[CGU]) | MATa his3Δ1 leu2Δ0 met15Δ0 ura3Δ0 |
| yYW0435 | Random Mutation for pLM495 of gene crtI (L[UUG]354M[AUG]) | MATa his3Δ1 leu2Δ0 met15Δ0 ura3Δ0 |
| yYW0436 | Random Mutation for pLM495 of gene crtI (I[AUC]19I[AUU], A[GCC]249A[GCU], L[CUU]261L[CUC], S[AGC]339G[GGC], V[GUG]344M[AUG], A[GCU]408S[UCU]) | MATa his3Δ1 leu2Δ0 met15Δ0 ura3Δ0 |

TABLE 1-continued

Yeast strains used in this study.

| Strain name | Description | Genotype |
| --- | --- | --- |
| yYW0437 | Random Mutation for pLM495 of gene crtI (I[AUC]19V[GUC], L[UUG]354I[CUG]) | MATa his3Δ1 leu2Δ0 met15Δ0 ura3Δ0 |
| yYW0438 | Random Mutation for pLM495 of gene crtI (E[GAA]122N[GAU]) | MATa his3Δ1 leu2Δ0 met15Δ0 ura3Δ0 |
| yYW0439 | Random Mutation for pLM495 of gene crtI (I[AUC]19I[AUA], S[AGU]316U[ACU]) | MATa his3Δ1 leu2Δ0 met15Δ0 ura3Δ0 |
| yYW0440 | Random Mutation for pLM495 of gene crtI (V[GUC]425V[GUA], A[GCA]444U[ACA]) | MATa his3Δ1 leu2Δ0 met15Δ0 ura3Δ0 |
| yYW0441 | Random Mutation for pLM495 of gene crtI with no mutation | MATa his3Δ1 leu2Δ0 met15Δ0 ura3Δ0 |
| yYW0442 | Random Mutation for pLM495 of gene crtI with no mutation | MATa his3Δ1 leu2Δ0 met15Δ0 ura3Δ0 |
| yYW0443 | Random Mutation for pLM495 of gene crtI (M[AUG]82L[UUG],A[GCU]468A[GCA]) | MATa his3Δ1 leu2Δ0 met15Δ0 ura3Δ0 |
| yYW0444 | Random Mutation for pLM495 of gene crtI (Y[UAU]226Y[UAC]) | MATa his3Δ1 leu2Δ0 met15Δ0 ura3Δ0 |
| yYW0462 | Bottom-up in vitro SCRaMbLEd plasmid with crtE crtI crtYB tHMG1 inserted | MATa his3Δ1 leu2Δ0 met15Δ0 ura3Δ0 CAN1::crtI-crtYB-crtE-LEU |
| yYW0463 | Bottom-up in vitro SCRaMbLEd plasmid with crtE crtI crtYB tHMG1 inserted | MATa his3Δ1 leu2Δ0 met15Δ0 ura3Δ0 CAN2::crtI-crtYB-crtE-LEU |
| yYW0464 | Bottom-up in vitro SCRaMbLEd plasmid with crtE crtI crtYB tHMG1 inserted | MATa his3Δ1 leu2Δ0 met15Δ0 ura3Δ0 CAN3::crtI-crtYB-crtE-LEU |

TABLE 2

Plasmids used in this study.

| Plasmid name | Description |
| --- | --- |
| pLM495 | Top-down initial plasmid |
| pYW0108 | Top-down in vitro SCRaMbLEd pLM495, recovered from yYW0212 |
| pYW0109 | Top-down in vitro SCRaMbLEd pLM495, recovered from yYW0213 |
| pYW0110 | Top-down in vitro SCRaMbLEd pLM495, recovered from yYW0214 |
| pYW0113 | Acceptor vector |
| pYW0120 | Universal donor vector |
| pYW0122 | crtI in pYW0120 |
| pYW0123 | crtE in pYW0120 |
| pYW0124 | crtYB in pYW0120 |
| pYW0125 | tHMG1 in pYW0120 |
| pYW0126 | ERG10 in pYW0120 |
| pYW0127 | ERG12 in pYW0120 |
| pYW0128 | ERG8 in pYW0120 |
| pYW0129 | MVD1 in pYW0120 |
| pYW0130 | ERG20 in pYW0120 |
| pYW0131 | BTS1 in pYW0120 |
| pYW0198 | ERG13 in pYW0120 |
| pYW0235 | Bottom-up initial plasmid |
| pYW0199 | Bottom-up in vitro SCRaMbLEd plasmid with tHMG1 inserted, recovered from yYW0303 |
| pYW0200 | Bottom-up in vitro SCRaMbLEd plasmid with crtYB inserted, recovered from yYW0304 |
| pYW0201 | Bottom-up in vitro SCRaMbLEd plasmid with crtE inserted, recovered from yYW0305 |
| pYW0202 | Bottom-up in vitro SCRaMbLEd plasmid with crtI inserted, recovered from yYW0306 |
| pYW0204 | Bottom-up in vitro SCRaMbLEd plasmid with ERG12 inserted, recovered from yYW0308 |
| pYW0205 | Bottom-up in vitro SCRaMbLEd plasmid with MVD1 inserted, recovered from yYW0309 |
| pYW0206 | Bottom-up in vitro SCRaMbLEd plasmid with ERG20 inserted, recovered from yYW0310 |
| pYW0207 | Bottom-up in vitro SCRaMbLEd plasmid with ERG10 inserted, recovered from yYW0311 |
| pYW0208 | Bottom-up in vitro SCRaMbLEd plasmid with ERG8 inserted, recovered from yYW0312 |
| pYW0209 | Bottom-up in vitro SCRaMbLEd plasmid with BTS1 inserted, recovered from yYW0313 |
| pYW0212 | Bottom-up in vitro SCRaMbLEd plasmid with crtI, ERG13 inserted, recovered from yYW0316 |
| pYW0213 | Bottom-up in vitro SCRaMbLEd plasmid with crtI, ERG12 inserted, recovered from yYW0317 |
| pYW0215 | Bottom-up in vitro SCRaMbLEd plasmid with crtYB, crtE inserted, recovered from yYW0319 |

TABLE 2-continued

Plasmids used in this study.

| Plasmid name | Description |
| --- | --- |
| pYW0216 | Bottom-up in vitro SCRaMbLEd plasmid with crtYB, tHMG1 inserted, recovered from yYW0320 |
| pYW0217 | Bottom-up in vitro SCRaMbLEd plasmid with crtI, BTS1 inserted, recovered from yYW0321 |
| pYW0218 | Bottom-up in vitro SCRaMbLEd plasmid with crtE, crtI and tHMG1 inserted, recovered from yYW0322 |
| pYW0230 | Bottom-up in vitro SCRaMbLEd plasmid with two crtI inserted, recovered from yYW0338 |
| pYW0259 | 36bp redesigned loxPsym* inserted after start codon of URA3 |
| pYW0260 | pEASY vector encoding 10 loxPysm sites with 100bp between adjacent loxPsym sites |
| pYW0261 | pEASY vector encoding 10 loxPysm sites with 500bp between adjacent loxPsym sites |
| pYW0262 | pEASY vector encoding 10 loxPysm sites with 1000bp between adjacent loxPsym sites |
| pYW0263 | Recovered plasmid from yYW0263 |
| pYW0264 | Recovered plasmid from yYW0264 |
| pYW0265 | Recovered plasmid from yYW0265 |
| pYW0268 | Top-down in vitro SCRaMbLEd pLM495, recovered from yYW0396 |
| pYW0270 | Top-down in vitro SCRaMbLEd pLM495, recovered from yYW0398 |
| pYW0271 | Top-down in vitro SCRaMbLEd pLM495, recovered from yYW0399 |
| pYW0272 | Top-down in vitro SCRaMbLEd pLM495, recovered from yYW0400 |
| pYW0273 | Top-down in vitro SCRaMbLEd pLM495, recovered from yYW0401 |
| pYW0275 | Top-down in vitro SCRaMbLEd pLM495, recovered from yYW0403 |
| pYW0276 | Top-down in vitro SCRaMbLEd pLM495, recovered from yYW0404 |
| pYW0277 | Top-down in vitro SCRaMbLEd pLM495, recovered from yYW0405 |
| pYW0278 | Top-down in vitro SCRaMbLEd pLM495, recovered from yYW0406 |
| pYW0279 | Top-down in vitro SCRaMbLEd pLM495, recovered from yYW0407 |
| pYW0280 | Top-down in vitro SCRaMbLEd pLM495, recovered from yYW0408 |
| pYW0281 | Top-down in vitro SCRaMbLEd pLM495, recovered from yYW0409 |
| pYW0282 | Top-down in vitro SCRaMbLEd pLM495, recovered from yYW0410 |
| pYW0283 | Top-down in vitro SCRaMbLEd pLM495, recovered from yYW0411 |
| pYW0292 | redesigned pLM495 with SalI inserted between two loxPsym sites |

The following will be recognized by those skilled in the art in view of the present disclosure.

Inserting 34 bp loxPsym sites in the 3' untranslated region (UTR) of nonessential genes in synthetic yeast chromosomes or at the boundary of transcription units has shown no detectable impact on the expression of neighboring genes[3, 25, 26]. The addition of loxPsym sites provides genetic flexibility and enables chromosome or pathway rearrangements mediated by Cre recombinase[13-27].

In this disclosure, top-down in vitro SCRaMbLE for construction of pathway structural variation library as applied to pathway flux optimization is demonstrated. Compared with other in vitro recombination methods, which mainly focus on single recombination events or one evolved enzyme[28-30], the top-down in vitro SCRaMbLE system achieves combinatorial rearrangements precisely between deliberately placed loxPsym sites to yield complex new genetic architecture in a loxPsym-enabled pathway or chromosome. Unlike random mutagenesis, the SCRaMbLE system uses functional modularity as the basic building block of variation, via copy number variation as well as changes to TU order and orientation. The diversity of the SCRaMbLEd DNA pool partly relies on the number of loxPsym sites in the initial construct, which can be varied as described further herein. The more building blocks that are involved, the more diverse the resulting SCRaMbLEd pool. The top-down in vitro SCRaMbLE system is a suitable way to generate combinatorial diversity of DNA constructs with no need for selectable markers.

The SCRaMbLE system promotes deletion, inversion and duplication events, making it an useful tool for studying evolution, in particular duplication events could readily lead to a gain of function[31]. In our 100 kb synIXR-BAC in vitro SCRaMbLE example, >70% of transformed E. coli cells shows new combinatorial structures (FIG. 9d). However, because the Cre Recombinase reaction goes to equilibrium, the frequency of cells carrying SCRaMbLEd sequences may be lower when there are fewer loxPsym sites in the initial constructs. Using a yeast centromere plasmid encoding the β-carotene pathway genes as a non-limiting example, we demonstrate the in vitro SCRaMbLE system described herein can be used to optimize biosynthetic pathway flux via rearrangement of pathway TUs. The production of β-carotene in yeast can be increased by duplication and inversion of crtI gene in the constructed pathway[18] (FIG. 2). The top-down in vitro SCRaMbLE method provides a high throughput way to reconstruct pathway structures. This is particularly useful to study genetic networks and gene interactions.

To circumvent the need to assemble a multi-TU pathway encoding loxPsym sites for top-down in vitro SCRaMbLE, we developed bottom-up in vitro SCRaMbLE. Using the β-carotene pathway as an example, we observed that the recombined DNA pool yielded diverse carotenoid production in yeast. The production of β-carotene was increased and fewer carotenoid intermediates were observed with additional copies of the crtI and tHMG1 genes. For strategy 1 (URA3 marker in the donor fragments), we observed insertion of two or three donor fragments into the acceptor vector with a >10% frequency. This ratio was increased (up to ~20%) by increasing the mole ratio of donor fragments to acceptor vector.

Figure 19:
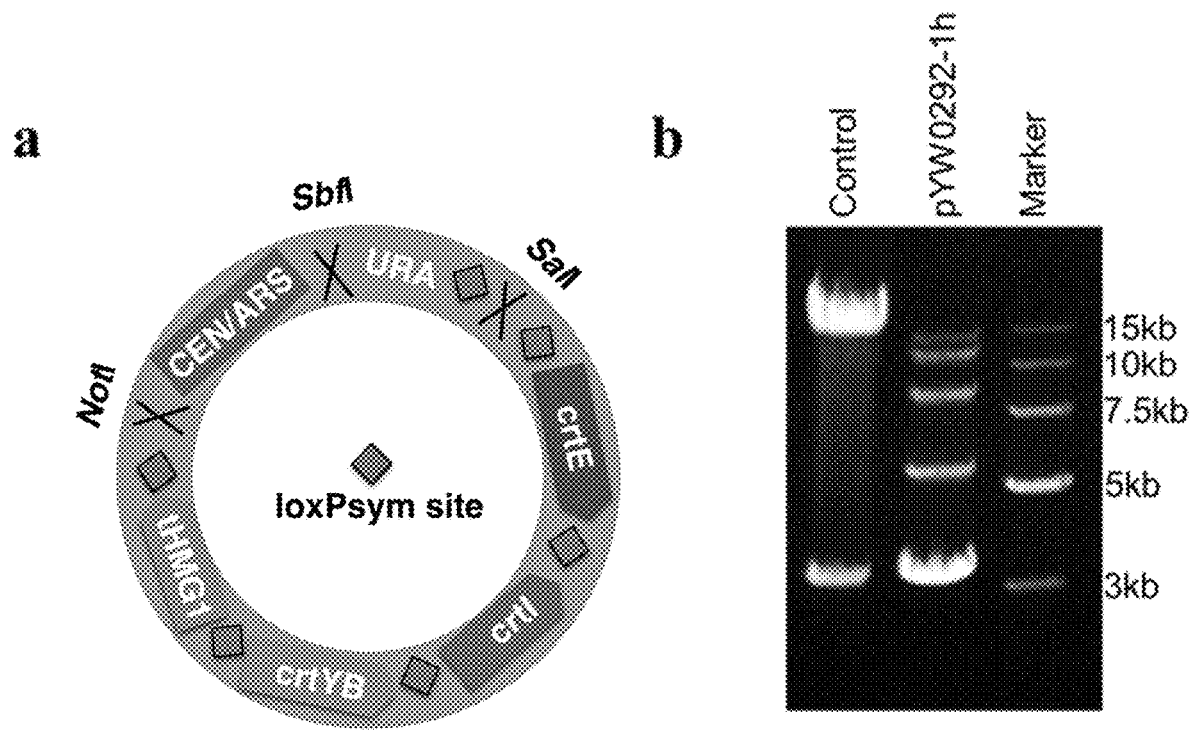
FIG. 19. Increased efficiency of in vitro SCRaMbLE using a redesigned pLM495 (pYW0292). (a) Map of the redesigned pLM495. A restriction enzyme cutting site (SalI) was inserted between two loxPsym sites. In this way, completely unSCRaMbLEd constructs can be linearized by SalI and cannot successfully transformation. (b) Agarose gel analysis of in vitro SCRaMbLE with pYW0292. The increased rate of truncated bands indicates increased efficiency of in vitro SCRaMbLE using this plasmid rather than the parental plasmid. Before transformed to *E. coli*, the SCRaMbLEd pool was digested by SalI. Both control and SCRaMbLEd plasmids were digested by NotI and SbfI before gel analysis.
Figure 20:
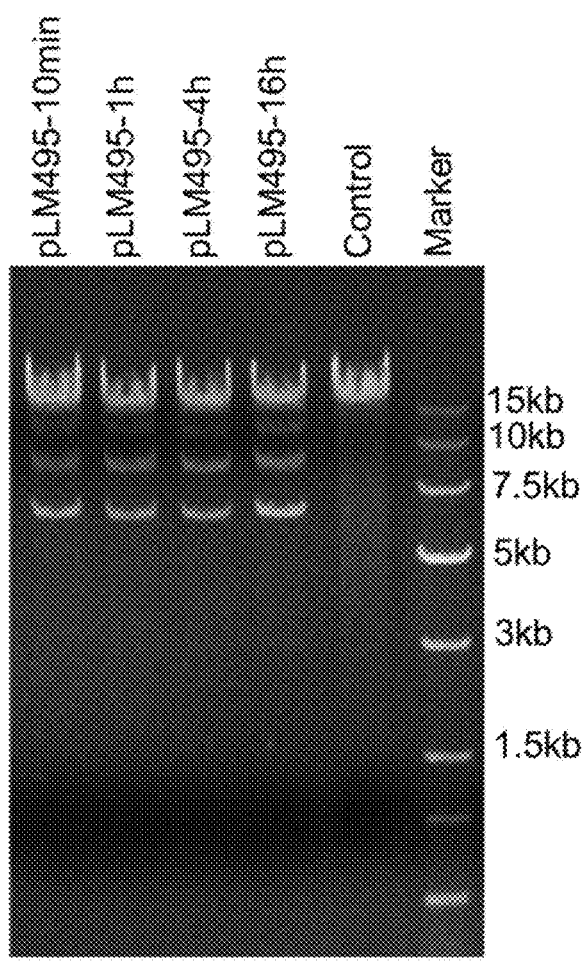
FIG. 20. Agarose gel analysis of in vitro SCRaMbLEd pLM495 time course. The in vitro SCRaMbLE reaction sampled at the indicated times. The SCRaMbLEd libraries were extracted from pool of SCRaMblEd *E. coli* colonies and then linearized by NotI. Marker, Trans 15k DNA Marker.

Together, the top-down and bottom-up in vitro SCRaMbLE systems provide a unique and efficient strategy to generate rearranged and optimized genetic structures. We have demonstrated that in vitro SCRaMbLE has several advantages over the in vivo method. 1) In vitro SCRaMbLE is highly controllable as compared to the in vivo reaction;

while the in vitro reaction can be stopped by heat inactivation, leaky Cre activity in vivo is a known problem and can lead to pathway and genome instability[13, 14]. 2) One can isolate sub-libraries with varied numbers of deleted building blocks by gel purification of digested SCRaMbLEd pools (FIG. 6). Here the efficiency of in vitro SCRaMbLE could be further optimized by identifying loss of a restriction enzyme cut site in the SCRaMbLEd construct (FIG. 19). 3) In vitro SCRaMbLE reactions reach equilibrium in 10 minutes and are stable for 16 hours (FIG. 20), whereas the in vivo reaction depends on ongoing expression of Cre recombinase. Deletion events accumulate with longer SCRaMbLE time, which can lead to reduced library complexity. 4) The phenotype-genotype analysis of in vitro SCRaMbLE is easier and more straightforward than in vivo because of less noise from the genome of host strains. 5) The in vitro SCRaMbLEd pool can be transformed into different host strains, further expanding the applicability of this method.

REFERENCES

This reference listing is not an indication that any of the references are material to patentability of this disclosure.

1. Galanie, S., et al., *Complete biosynthesis of opioids in yeast*. Science, 2015. 349(6252): p. 1095-1100.
2. Richardson, S. M., et al., *Design of a synthetic yeast genome*. Science, 2017. 355(6329): p. 1040-1044.
3. Wu, Y., et al., *Bug mapping and fitness testing of chemically synthesized chromosome X*. Science, 2017. 355 (6329).
4. Gibson, D. G., et al., *Creation of a bacterial cell controlled by a chemically synthesized genome*. Science, 2010. 329(5987): p. 52-6.
5. Hutchison, C. A., 3rd, et al., *Design and synthesis of a minimal bacterial genome*. Science, 2016. 351(6280): p. aad6253.
6. Guo, F., D. N. Gopaul, and G. D. Van Duyne, *Structure of Cre recombinase complexed with DNA in a site-specific recombination synapse*. Nature, 1997. 389(6646): p. 40-46.
7. Nagy, A., *Cre recombinase: the universal reagent for genome tailoring*. genesis, 2000. 26(2): p. 99.
8. Zou, Y.-R., et al., *Cre-loxP-mediated gene replacement: a mouse strain producing humanized antibodies*. Current Biology, 1994. 4(12): p. 1099-1103.
9. Lewandoski, M. and G. R. Martin, *Cre-mediated chromosome loss in mice*. Nature genetics, 1997. 17(2): p. 223-225.
10. Marsischky, G. and J. LaBaer, *Many paths to many clones: a comparative look at high-throughput cloning methods*. Genome research, 2004. 14(10b): p. 2020-2028.
11. Parks, R., et al., *A high-efficiency Cre/loxP-based system for construction of adenoviral vectors*. Human gene therapy, 1999. 10(16): p. 2667-2672.
12. Hoess, R. H., A. Wierzbicki, and K. Abremski, *The role of the loxP spacer region in P1 site-specific recombination*. Nucleic acids research, 1986. 14(5): p. 2287-2300.
13. Shen, Y., et al., *SCRaMbLE generates designed combinatorial stochastic diversity in synthetic chromosomes*. Genome research, 2016. 26: p. 36-49.
14. Dymond, J. S., et al., *Synthetic chromosome arms function in yeast and generate phenotypic diversity by design*. Nature, 2011. 477(7365): p. 471-6.
15. Annaluru, N., et al., *Total synthesis of a functional designer eukaryotic chromosome*. Science, 2014. 344 (6179): p. 55-58.
16. Dejana, J., B. A. Blount, and E. Tom, *Total synthesis of a eukaryotic chromosome: Redesigning and SCRaMbLE-ing yeast*. Bioessays News & Reviews in Molecular Cellular & Developmental Biology, 2014. 36(9): p. 855.
17. Mercy, G., et al., *3D organization of synthetic and scrambled chromosomes*. Science, 2017. 355(6329).
18. Verwaal, R., et al., *High-level production of beta-carotene in Saccharomyces cerevisiae by successive transformation with carotenogenic genes from Xanthophyllomyces dendrorhous*. Appl Environ Microbiol, 2007. 73(13): p. 4342-50.
19. Mitchell, L. A., et al., *Versatile genetic assembly system (VEGAS) to assemble pathways for expression in S. cerevisiae*. Nucleic Acids Res, 2015. 43(13): p. 6620-30.
20. Mitchell, L. A., et al., *qPCRTag Analysis—A High Throughput, Real Time PCR Assay for Sc2.0 Genotyping*. Journal of visualized experiments: JoVE, DOI: 10.3791/52941, 2015: p. e52941-e52941.
21. Cirino, P. C., K. M. Mayer, and D. Umeno, *Generating mutant libraries using error-prone PCR*. Methods in Molecular Biology, 2003. 231: p. 3.
22. Zhang, X., et al., *Atmospheric and room temperature plasma (ARTP) as a new powerful mutagenesis tool*. Applied Microbiology & Biotechnology, 2014. 98(12): p. 5387.
23. Agmon, N., et al., *Yeast Golden Gate (yGG) for the efficient assembly of S. cerevisiae transcription units*. ACS synthetic biology, 2015. 4(7): p. 853-859.
24. Boeke, J. D., F. LaCroute, and G. R. Fink, *A positive selection for mutants lacking orotidine-5'-phosphate decarboxylase activity in yeast: 5-fluoro-orotic acid resistance*. Molecular & general genetics, 1984. 197: p. 345-346.
25. Xie, Z. X., et al., *"Perfect" designer chromosome V and behavior of a ring derivative*. Science, 2017. 355(6329).
26. Mitchell, L. A., et al., *Synthesis, debugging, and effects of synthetic chromosome consolidation: synVI and beyond*. Science, 2017. 355(6329).
27. Dymond, J. and J. Boeke, *The Saccharomyces cerevisiae SCRaMbLE system and genome minimization*. Bioengineered, 2012. 3(3): p. 170-173.
28. Stemmer, W. P., *DNA shuffling by random fragmentation and reassembly: in vitro recombination for molecular evolution*. Proceedings of the National Academy of Sciences, 1994. 91(22): p. 10747-10751.
29. Coco, W. M., et al., *DNA shuffling method for generating highly recombined genes and evolved enzymes*. Nature biotechnology, 2001. 19(4): p. 354-359.
30. Hartley, J. L., G. F. Temple, and M. A. Brasch, *DNA cloning using in vitro site-specific recombination*. Genome research, 2000. 10(11): p. 1788-1795.
31. Innan, H. and F. Kondrashov, *The evolution of gene duplications: classifying and distinguishing between models*. Nature Reviews Genetics, 2010. 11(2): p. 97-108.
32. Sambrook, J. and D. W. Russell, *Isolation of BAC DNA from small-scale cultures*. Cold Spring Harbor Protocols, 2006. 2006(1): p. pdb. prot4006.

What is claimed is:

1. An in vitro method for making a recombinant DNA molecule comprising:
   i) combining in vitro:
   a recombination-site-mediated evolution (a SCRaMbLE) ready DNA polynucleotide comprising at least one transcription unit (TU), the SCRaMbLE ready DNA polynucleotide comprising introduced site-specific recombinase recognition sites that can be recognized by a recombinase, with
   ii) a recombinase that recognizes the site-specific recombinase recognition sites;
   such that the polynucleotide is recombined to provide a recombined polynucleotide; and optionally determining the sequence, and/or determining the expression of the recombined polynucleotide subsequent to introducing the recombined polynucleotide into a microorganism.

2. The method of claim 1, wherein the site-specific recombinase recognition sites are loxPsym sites, and wherein the recombinase recognizes the loxPsym sites.

3. The method of claim 2, wherein the SCRaMbLE ready DNA comprises more than one TU.

4. The method of claim 3, wherein at least one TU comprises a sequence that encodes a non-coding RNA.

5. The method of claim 3, wherein more than at least two TUs encode distinct proteins.

6. The method of claim 5, wherein the distinct proteins participate in a same metabolic pathway and/or encode distinct proteins that form a multi-protein complex in vitro or in vivo.

7. The method of claim 2, wherein a TU comprises a sequence that encodes a protein.

8. The method of claim 1, wherein the recombinant polynucleotide comprises an inversion and/or a deletion of a segment of the SCRaMbLE ready DNA polynucleotide that was present in the SCRaMbLE ready DNA prior to combining the SCRaMbLE ready DNA with the recombinase.

9. The method of claim 1, wherein activity of the recombinase is stopped by manipulating the in vitro reaction by application of heat or a denaturing or chelating agent.

10. The method of claim 1, further comprising introducing the recombined polynucleotide into a microorganism to obtain a modified microorganism, and determining function of the TUs by analysis of the modified microorganism.

11. The method of claim 10, wherein the modified microorganism is a yeast.

12. The method of claim 1, further comprising determining the sequence of the recombined polynucleotide.

* * * * *